(12) United States Patent
Tran et al.

(10) Patent No.: US 7,699,056 B2
(45) Date of Patent: Apr. 20, 2010

(54) MEDICAL DEVICES AND METHODS OF MAKING AND USING SUCH DEVICES

(75) Inventors: Quang Tran, Redwood City, CA (US); Christopher A. Stout, San Mateo, CA (US); Elisa J. Aldridge, Menlo Park, CA (US); Betsy Swann, Grass Valley, CA (US)

(73) Assignee: Conceptus, Inc., Mountain View, CA (US)

( * ) Notice: Subject to any disclaimer, the term of this patent is extended or adjusted under 35 U.S.C. 154(b) by 878 days.

(21) Appl. No.: 10/866,493

(22) Filed: Jun. 10, 2004

(65) Prior Publication Data

US 2005/0274384 A1    Dec. 15, 2005

(51) Int. Cl.
*A61F 6/06* (2006.01)
*A61F 6/14* (2006.01)
*A61F 13/00* (2006.01)
*A61M 1/00* (2006.01)
*A61M 5/178* (2006.01)

(52) U.S. Cl. .............. 128/831; 128/830; 128/832; 128/833; 128/839; 604/27; 604/28; 604/36; 424/422; 424/430

(58) Field of Classification Search ......... 128/830–841; 623/1; 604/28, 53, 32, 36, 38, 108, 158, 604/213; 606/32, 36, 38, 41, 108, 158, 213, 606/28, 53; 424/422, 426, 430
See application file for complete search history.

(56) References Cited

U.S. PATENT DOCUMENTS

| 4,994,069 A | | 2/1991 | Ritchart et al. |
| 5,095,917 A | * | 3/1992 | Vancaillie .................... 128/831 |
| 5,250,071 A | * | 10/1993 | Palermo ..................... 606/198 |
| 5,312,415 A | * | 5/1994 | Palermo ..................... 606/108 |

(Continued)

FOREIGN PATENT DOCUMENTS

EP        O 570 102 A     11/1993

(Continued)

OTHER PUBLICATIONS

PCT International Search Report and Written Opinion for PCT International Appln No. PCT/US2005/020533, mailed Dec. 27, 2005. (21 pages).

(Continued)

*Primary Examiner*—Patricia M Bianco
*Assistant Examiner*—Brandon Jackson
(74) *Attorney, Agent, or Firm*—Blakely, Sokoloff, Taylor & Zafman LLP

(57) ABSTRACT

Devices, such as medical devices for inhibiting conception, and methods of using and/or making these devices. In one aspect of the disclosure, a medical device has a delivery system and a first insert, which is removably coupled to the delivery system and which is designed to be deployed within a portion of a first fallopian tube, and a second insert, which is removably coupled to the delivery system and which is designed to be deployed within a portion of a second fallopian tube. Other aspects of the disclosure include, among other things, inserts made from one or more polymers; inserts which are designed to pierce and remain in place; and inserts which are implanted through a fluid delivery system.

12 Claims, 29 Drawing Sheets

U.S. PATENT DOCUMENTS

| | | | |
|---|---|---|---|
| 5,496,294 A * | 3/1996 | Hergenrother et al. | 604/524 |
| 5,733,329 A | 3/1998 | Wallace et al. | |
| 5,752,974 A | 5/1998 | Rhee et al. | |
| 5,800,455 A * | 9/1998 | Palermo et al. | 606/191 |
| 5,935,137 A | 8/1999 | Saadat et al. | |
| 6,494,896 B1 | 12/2002 | D'Alessio et al. | |
| 6,526,979 B1 | 3/2003 | Nikolchev et al. | |
| 6,634,361 B1 | 10/2003 | Nikolchev et al. | |
| 6,695,832 B2 * | 2/2004 | Schon et al. | 604/544 |
| 2001/0041900 A1 | 11/2001 | Callister et al. | |
| 2002/0013589 A1 | 1/2002 | Callister et al. | |
| 2002/0055666 A1 * | 5/2002 | Hunter et al. | 600/1 |
| 2003/0051735 A1 | 3/2003 | Pavcnik et al. | |

FOREIGN PATENT DOCUMENTS

| | | |
|---|---|---|
| WO | WO 99/15116 | 4/1999 |
| WO | WO 01/13832 A1 | 3/2001 |
| WO | WO 02/15796 A2 | 2/2002 |
| WO | WO 02/17771 A2 | 3/2002 |

OTHER PUBLICATIONS

PCT Notification Concerning Transmittal of the International Preliminary Report on Patentability; PCT International Preliminary Report on Patentability; and PCT Written Opinion of the International Searching Authority for PCT/US2005/020533, mailed Dec. 28, 2006. (13 pages).

* cited by examiner

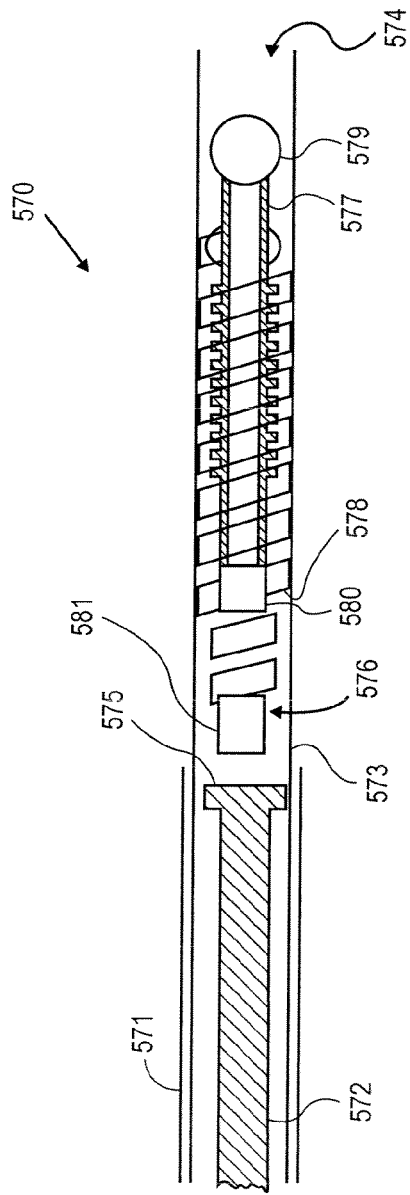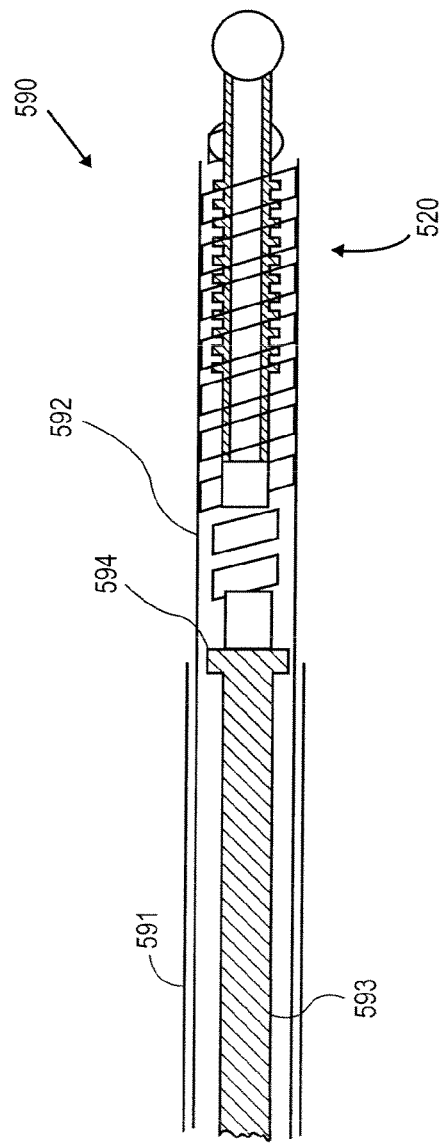
FIG. 12D
FIG. 12E

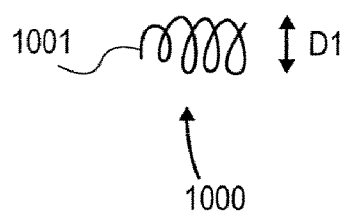
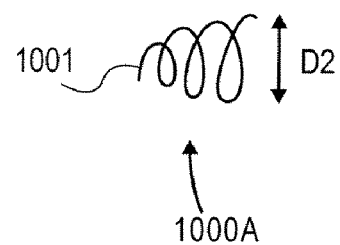
FIG. 22A
FIG. 22B
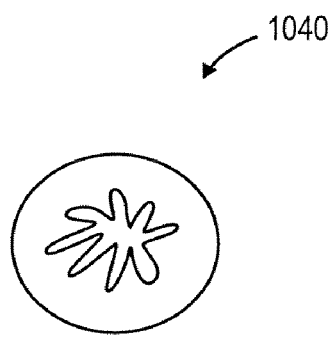
FIG. 23A
FIG. 23B

MEDICAL DEVICES AND METHODS OF MAKING AND USING SUCH DEVICES

BACKGROUND OF THE INVENTION

This description relates generally to medical devices, such as medical devices for contraception and/or sterilization or occlusion, or other types of treatments, of body lumens for other medical purposes. Certain embodiments of the present invention relate to intrafallopian contraceptive implants or insert devices and non-surgical methods for the delivery of such devices.

Many of the presently available contraception methods require significant user involvement, and user non-compliance results in high rates of failure. While the theoretical effectiveness of existing contraceptives, including barrier methods and hormonal therapies, is well established, overcoming user non-compliance to improve overall efficacy has proven difficult. Thus, it is often desirable to seek a method of permanent sterilization. Traditional methods for permanent sterilization include fallopian tube ligation and vasectomy. These methods are invasive, surgical procedures which are undesirable to some people and not available to many people in the world.

One alternative to conventional contraceptive methods is to transcervically introduce an object (e.g. a coil) into a fallopian tube to inhibit conception. Devices, systems and methods for such a contraceptive approach have been described in various patents and patent applications assigned to the present assignee. For example, PCT patent application No. 99/15116 and U.S. Pat. No. 6,526,979 and U.S. Pat. No. 6,634,361 describe devices which are transcervically inserted into an ostium of a fallopian tube and mechanically anchored within the fallopian tube. The devices described in these patents and patent applications may promote a tissue ingrowth around and within the inserted device, which may be referred to as an implant or an insert. One example of such devices is the device known as "Essure" from Conceptus, Inc. of San Carlos, Calif. This tissue ingrowth tends to provide long term contraception and/or permanent sterilization without the need for surgical procedures. Another device is described in U.S. Pat. No. 5,095,917.

SUMMARY

Various different embodiments are disclosed below and the following summary provides a brief description of only some of these embodiments. According to one aspect of the invention, certain embodiments described below relate to a medical device for use in a patient having a first fallopian tube and a second fallopian tube. The device includes a delivery system, and a first insert removably coupled to the delivery system, wherein the first insert is designed to be deployed within a portion of the first fallopian tube and is formed at least in part from a non-biodegradable material (e.g. a metal or a non-biodegradable polymer). The device further includes a second insert removably coupled to the delivery system, wherein the second insert is designed to be deployed within a portion of the second fallopian tube and is formed at least in part from a non-biodegradable material (e.g. a metal or a non-biodegradable polymer). In one particular exemplary embodiment, the delivery system includes an outer sheath and a release catheter coaxially disposed within the outer sheath and a lumen disposed within the release catheter, wherein the first insert and the second insert are serially disposed within the lumen, thereby allowing a single delivery system to be used to deliver an insert for each of the two fallopian tubes in a patient. Various different types of implants or inserts may be used with this embodiment, including fully or partially molded inserts, or metal, stentlike inserts or inserts designed with two concentrically positioned coils, such as metal coils.

According to another aspect of the invention, certain embodiments described below relate to a device for inhibiting conception in a patient, wherein the device includes a delivery system and a structure having a piercing end designed to pierce a portion of the fallopian tube and to remain attached to the portion. This structure is detachably coupled to the delivery system and has a first configuration prior to piercing the portion and forms a second configuration upon or after piercing the portion. The structure typically includes at least one agent attached to the structure which is designed to cause a tissue ingrowth into the fallopian tube. In certain embodiments, the structure is designed to pierce the portion and then bend proximally or distally away from the portion to form the second configuration. Methods for using such a device are also described.

According to another aspect of the invention, certain embodiments involve the formation of an insert for inhibiting conception in a patient having at least one fallopian tube. A method for formation includes forming an insert which includes a non-biodegradable polymer and which is designed to be implanted into a fallopian tube and inserting the insert into a delivery system. Devices relating to this aspect are also described below, such as a device which comprises a non-biodegradable polymer and which is designed to be implanted into a fallopian tube. The insert which includes the polymer is removably coupled to a delivery system for delivery into the fallopian tube. In certain embodiments, the insert which includes a polymer may be formed by either a molding operation or an extrusion operation.

According to another aspect of the invention, certain exemplary embodiments of a device for inhibiting conception include a delivery system, a lumen coupled to the delivery system, an insert removably disposed in the lumen, wherein the insert is sized to be deployed in a fallopian tube, and a fluid input port coupled to said lumen, where the fluid input port is designed to receive a fluid, such as a liquid or a gas, to expel the insert through an outlet of the lumen and into the fallopian tube. A method of delivering such an insert through the introduction of a fluid is also described.

Various other devices and methods for using devices, including kits for use in treating patients, are also described below. Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings in which like references indicate similar elements.

FIG. 12D is a cutaway side view of a delivery system which uses an insert which is similar to the insert shown in FIG. 12A.

FIG. 12E shows the delivery system of FIG. 12D after a delivery sheath has been partially retracted relative to the insert.

FIG. 15 shows a distal portion of such a delivery system.

FIG. 22A shows a side view of an insert coil in a first configuration, and FIG. 22B shows that same coil in a second configuration which is expanded radially relative to the coil's configuration shown in FIG. 22A.

FIGS. 23A and 23B show a before and after view of a fallopian tube, shown in cross-sectional views, wherein the fallopian tube has a more open configuration in FIG. 23B as a result of the use of a delivery system which injects a fluid, such as the delivery system shown in FIG. 21.

DETAILED DESCRIPTION

The subject invention will be described with reference to numerous details set forth below, and the accompanying drawings will illustrate the invention. The following description and drawings are illustrative of the invention and are not to be construed as limiting the invention. Numerous specific details are described to provide a thorough understanding of the present invention. However, in certain instances, well known or conventional details are not described in order to not unnecessarily obscure the present invention in detail.

The various aspects of the present inventions provide devices and methods to inhibit pregnancy, typically for the long term inhibition of pregnancy, and often providing permanent contraception or sterilization. Examples of contraceptive devices and methods for using these devices with delivery systems are provided in U.S. Pat. No. 6,526,979 and U.S. Pat. No. 6,634,361, both of which are incorporated herein by reference.

Figure 1:
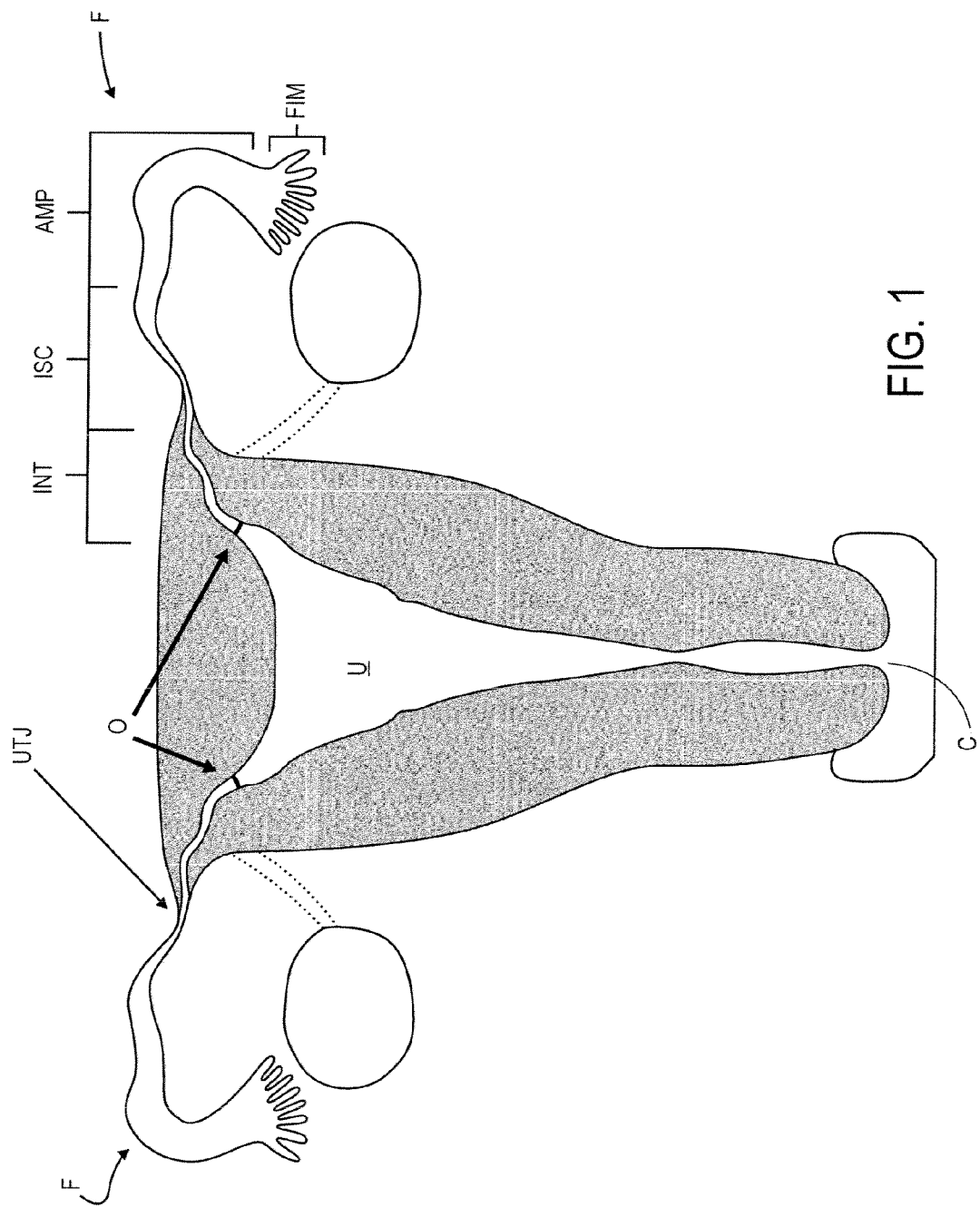
FIG. 1 illustrates the uterine and tubal anatomy for deployment of the contraceptive devices described herein.

FIG. 1 is a diagram of a female reproductive tract. Referring to FIG. 1, access to uterus U will generally be gained through cervix C. From within uterus U, fallopian tubes F are accessed via tubal ostia O. Fallopian tubes F generally include three segments between ostium O and the fimbria FIM. The intramural segment INT of fallopian tubes F are surrounded by the muscular uterine tissues. Beginning at uterotubal junction UTJ, fallopian tubes F extend beyond the uterine tissues and within the peritoneal cavity along an isthmic segment ISC and then along an ampullary segment AMP.

In general, a desired placement for intrafallopian contraceptive devices such as those described in the above noted patents, is a location which spans an intramural INT to the isthmic ISC portion of the fallopian tube. Where a radially expandable attachment mechanism such as an outer coil is included on the intrafallopian contraceptive device, the expandable or anchoring structure may preferably span the uterotubal junction UTJ. It should be noted that the uterotubal junction UTJ may be defined as the plane where the fallopian tube meets the peritoneal cavity.

An exemplary contraceptive delivery system will preferably be able to accommodate a wide variety of anatomies. Two factors contribute to the importance of this variability. First, a wide variation may be observed between tubal anatomies of differing patients. Secondly, it can be quite difficult to determine and identify the specific tubal anatomy of a particular patient.

Generally, methods for delivery of a contraceptive device in which the delivery systems described herein or in the previously noted patents will be used involve positioning the distal end of the catheter or system at a desired location in or near a fallopian tube, freeing a contraceptive device from the catheter or system, and removing the catheter or system from the fallopian tube, leaving behind the contraceptive device.

Figure 2:
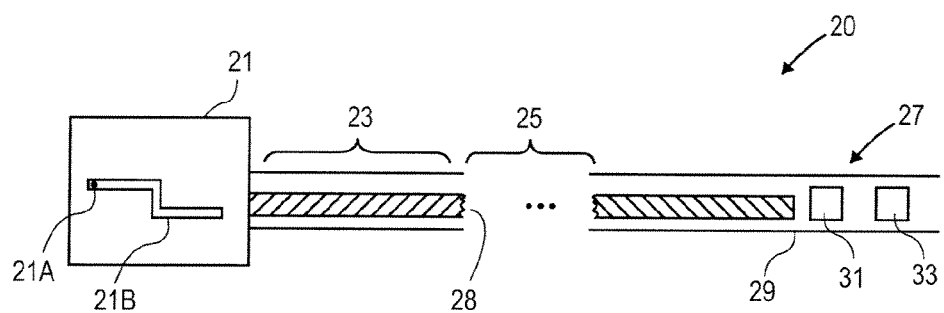
FIG. 2 shows a cross-sectional view of a delivery system having two inserts serially loaded into a delivery lumen, where the delivery system includes a proximal control 21.

FIG. 2 shows one aspect of certain embodiments of the present invention in which a delivery system 20 includes two serially disposed inserts 31 and 33 within a lumen of a delivery catheter 29. Also disposed within the lumen is a rod 28. The delivery system as shown in FIG. 2 includes a proximal portion 23, a middle portion 25 and a distal portion 27. The distal portion 27 includes the serially disposed inserts 31 and 33. A proximal control 21 is coupled to the proximal portion 23 of the delivery system in order to control the release of the two inserts by movement of a knob 21A within a slot 21B on the proximal control 21. The knob 21A may in one embodiment be coupled to the rod 28, causing the rod 28 to move longitudinally relative to the delivery catheter 29 within the lumen of the delivery catheter 29 in order to push out each insert, one at a time. This may be performed by moving the knob 21A from left to right as shown in FIG. 2. The slot 21B is formed with two longitudinal sections which are parallel with the longitudinal direction of the delivery system 20, and the slot 21B includes a transverse section coupling the two longitudinal sections. This allows easy control so that the control knob 21A may be moved through the first longitudinal length from left to right (in the upper portion of the slot) in order to push out the first insert 33, and then without moving any further the insert 31, the knob 21A may be pushed down into the lower portion of the slot 21B to then push out the second insert, which is insert 31. The two portions of the slot 21B which are separated by the transverse portions allow for the controlled dispensing of the two inserts without risk of pushing out both inserts when the physician desires to push out only one. It will be appreciated that in an alternative embodiment, a knob on a slot may be used to control the longitudinal movement of the delivery sheath relative to a stationary rod such that as the sheath is retracted towards the proximal portion, the first implant is exposed and thereby released from the delivery catheter, and as the sheath is further pulled back towards the proximal portion and towards the proximal control, a second insert is exposed and thereby deployed from the delivery catheter. This particular alternative embodiment is disclosed further in connection with FIG. 4 which is described below. It will also be appreciated that numerous other alternative control mechanisms may be used rather than those shown and described herein.

Figure 3:
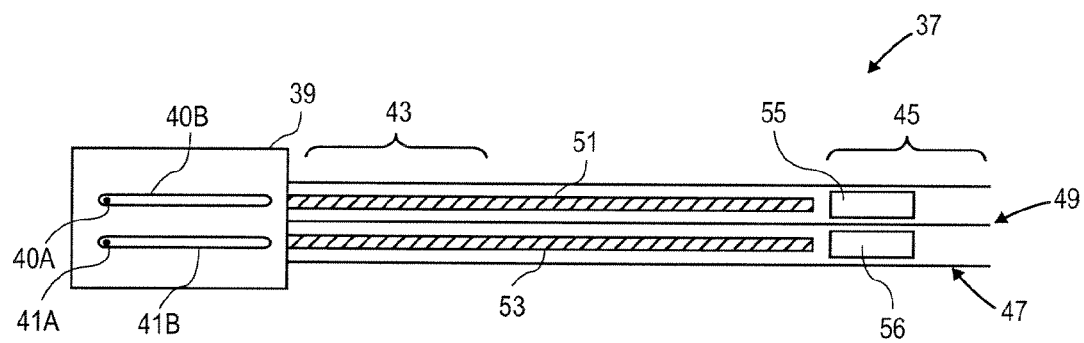
FIG. 3 shows a cross-sectional view of a delivery system having two inserts and being coupled to a proximal control 39.

The delivery system shown in FIG. 3 does not use a serially disposed set of inserts. Rather, the inserts are loaded into separate lumens which are separated by the separator 49 as shown in FIG. 3. The delivery system 37 of FIG. 3 includes a proximal portion 43 which is coupled to a proximal control 39 and a distal portion 45 in which the two inserts, insert 55 and insert 56, are inserted into the two lumens in the delivery system 37. A first rod 51 is disposed within the same lumen as the first insert 55, and second rod 53 is disposed within the same lumen as the second insert 56. A delivery sheath 47 surrounds both rods and both inserts. The rods in the case of FIG. 3 serve as push rods which move relative to a stationary delivery sheath 47. Each rod is actuated and moveable by a separate knob on the proximal control 39. The first knob 40A is movably disposed within a first slot 40B. The first knob 40A is coupled to and controls the longitudinal movement of the rod 51 such that the rod 51 can be used to push the insert 55 out of the delivery system 37. Similarly, the second rod 53 is coupled to the knob 41A which is moveable relative to the slot 41B to cause the push rod to push out the insert 56 relative to a stationary delivery sheath 47.

It can be seen that the delivery systems 20 and 37 of FIGS. 2 and 3 provide two methods of using a single delivery catheter to deliver two different inserts, one for each fallopian tube. This allows the physician to use the same delivery system for two different fallopian tubes rather than having to insert a second delivery system for the second fallopian tube. Thus it is anticipated that the time required and the cost of such an operation will be reduced as a result of being able to use a single delivery system rather than two separate delivery systems, each with their own insert. It will be appreciated that these delivery systems 20 or 37 may be used on a patient who has only one fallopian tube.

Figure 4:
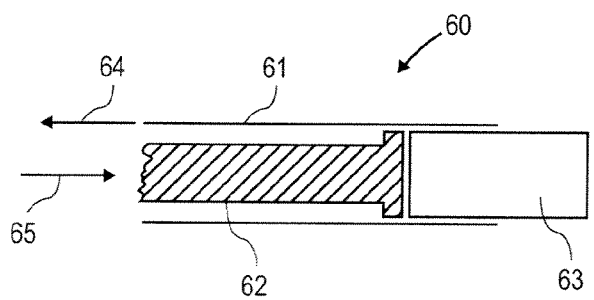
FIG. 4 shows a cross-sectional view of a distal portion of a delivery system such as that shown in either FIG. 2 or 3.

FIG. 4 shows the distal portion of a delivery system 60 which includes an insert 63 at the distal end of the delivery system 60. A delivery sheath 61 partially surrounds a portion of the insert 63 such that the insert is within the lumen of the delivery sheath 61. A rod 62 is also within this lumen of the delivery sheath 61 and is shown in near contact with the insert 63. FIG. 4 illustrates the two possible mechanisms of deploying the insert 63. In the case of the arrow 65, the rod 62 acts as a push rod and moves relative to a stationary delivery sheath 61 to push the insert out of the distal end of the lumen which contains the rod 62. In an alternative embodiment, shown by the arrow 64, the delivery sheath 61 may be retracted relative to a stationary rod 62 such that the insert 63 is exposed by the removal of the delivery sheath, thereby allowing the insert 63 to be released from the delivery system 60 and be deployed in a desired position. This occurs by moving the delivery sheath relative to a stationary rod. It will be appreciated that in yet another alternative embodiment, there is a push rod which moves distally away from the proximal control and a retracting sheath which moves proximally towards the proximal control, which may be together utilized in one embodiment in order to deploy an insert or several inserts.

Figure 5A:
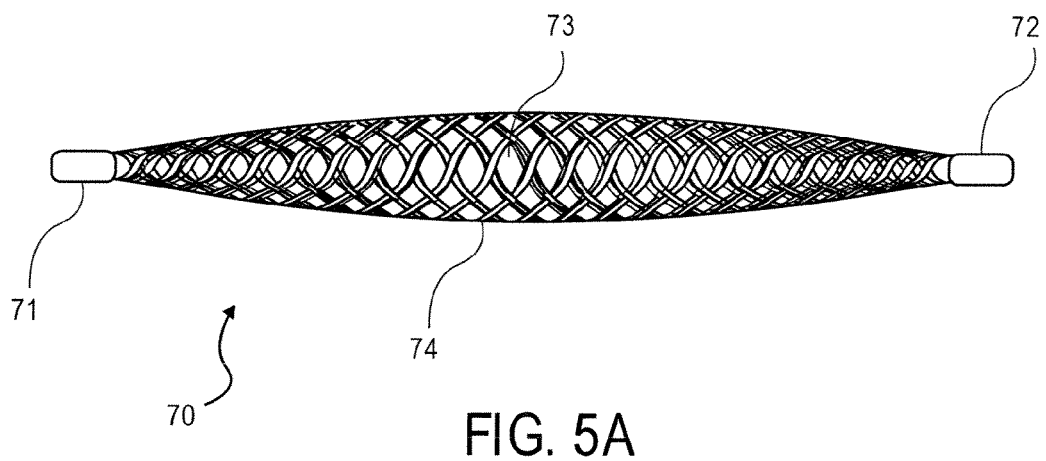
FIG. 5A shows an example of an insert or implant which may be used in certain embodiments of the invention and FIG. 5B shows another example of an insert or implant which may be used in certain embodiments of the invention and FIG. 5C shows another example of an insert or implant.

FIG. 5A shows a top view of one particular exemplary insert which resembles a braided stent that has a frame 74 which surrounds an inner portion which may be hollow or may be filled with a mesh or other tissue ingrowth agents. The ends of the frame 74 are capped by ends 71 and 72 as shown in FIG. 5A. The insert 70 may be formed from metal such as stainless steel or a superelastic or shape memory material such as a nickel titanium (NiTi) alloy such as nitinol, or platinum, or tantalum, or gold, or rigid or semi-rigid biocompatible plastics. In one particular embodiment, the insert 70 may be formed at least in part from a superelastic material providing a controlled force on the body lumen such as a portion of the fallopian tube during expansion of the insert. The insert may expand radially from a first diameter to a second diameter which is larger than the first diameter. The insert may be delivered by a delivery system (e.g. a delivery catheter) which constrains the insert to the size of the first diameter and after the insert is deployed, it may expand to the second diameter which at least slightly exceeds the diameter of a lumen of the fallopian tube. The material or materials of the insert may be superelastic so that the insert can expand in a manner that causes it to resiliently apply an anchoring force against the wall of the fallopian tube, thereby resisting against being expelled by the fallopian tube. The surface of the insert may be designed to facilitate epithelial growth; one way of doing this is to provide the insert with an open or latticelike framework to promote and support epithelial growth into as well as around the insert to ensure secure attachment to an embodiment within the wall of the body lumen. The open, hollow inner portion 73 within the frame 74 may include a tissue ingrowth agent such as a polyester fiber (e.g. polyethylene terephthalate) or other materials known to facilitate fibrotic or epithelial growth. The surface of the frame may also be modified or treated or include such a tissue ingrowth material. The surface modification may include plasma deposition or laser drilling or photochemical etching or sintering and the like. Further, increasing the surface area of the frame by such surface modification techniques (e.g. surface drilling or etching or sintering) can also provide greater adhesion for the epithelial tissue. Suitable surface treatments include plasma etching, sandblasting, machining and other treatments to roughen the surface. In other embodiments, the device may be coated or seeded to spur epithelialization. For example, the device can be coated with a polymer having impregnated therein a drug, enzyme or protein for inducing or promoting epithelial tissue growth. Any of these various techniques for including a tissue ingrowth agent may be used with the various other inserts shown or described herein.

Figure 5B:
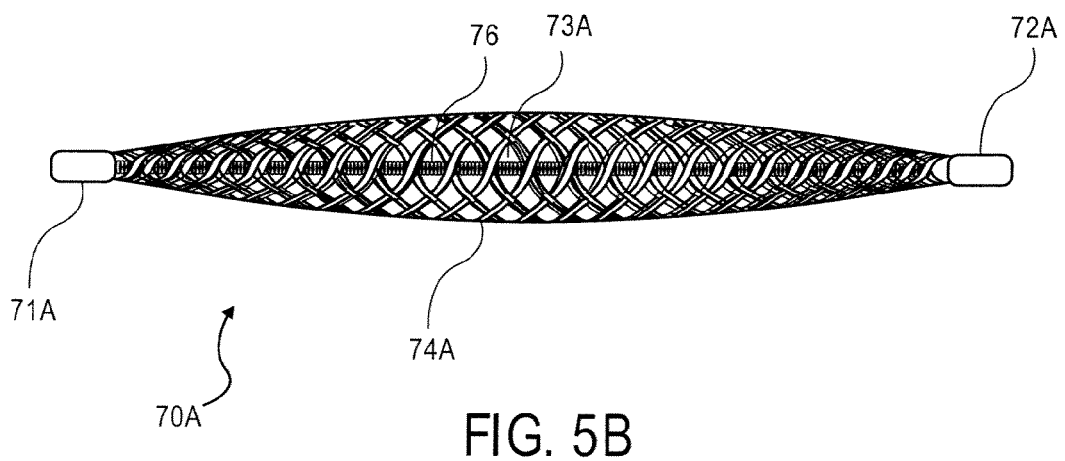

FIG. 5B shows a top view of another exemplary insert 70A which is similar to insert 70 except that insert 70A includes an inner member (e.g. a coil 76) which is surrounded by the braided frame 74A and which is attached to ends 71A and 72A. The coil 76 is disposed within the open, hollow inner portion 73A which is also surrounded by the braided frame 74A. The open, hollow inner portion 73A may include a tissue ingrowth agent such as a polyester fiber or fibers (e.g. polyethylene terephthalate) or other materials known to facilitate fibrotic or epithelial growth. The insert 70A may be formed from the same materials as insert 70 and may be deployed and operate in the same manner as insert 70. For example, the insert 70A may be formed at least in part from a superelastic material which provides a resilient anchoring force against the wall of a fallopian tube and it may expand radically from a first diameter, prior to deployment from a delivery system, to a second diameter after deployment from the delivery system, where the second diameter is larger than the first diameter.

Figure 5C:
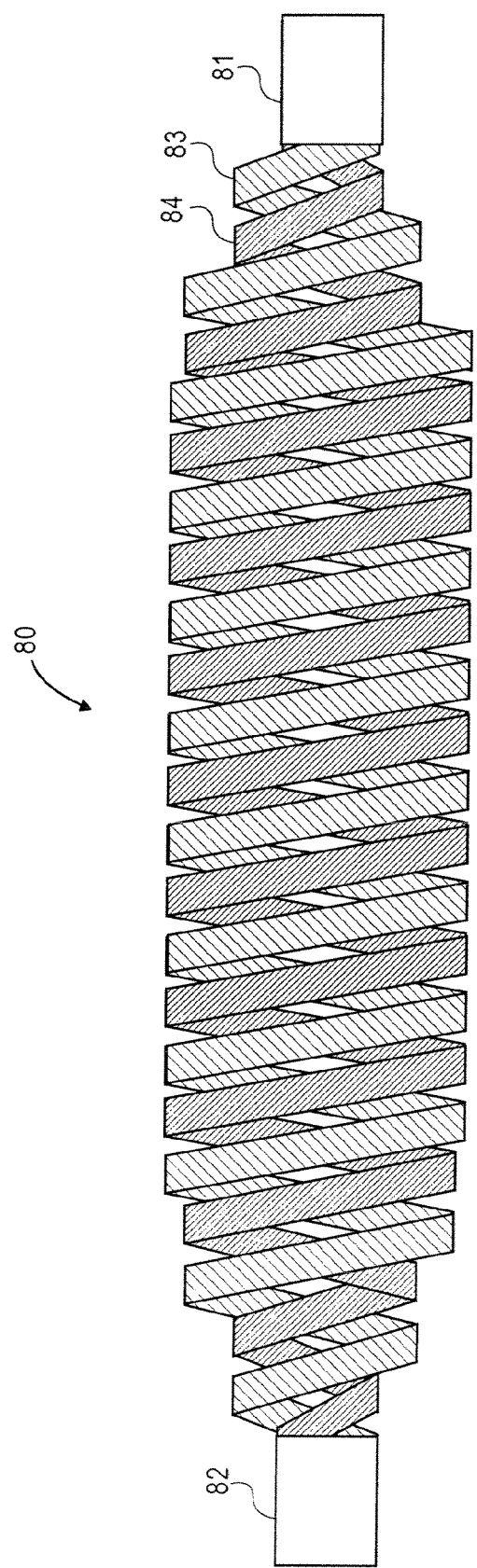

FIG. 5C shows a top view of another exemplary insert 80 which includes two coils 83 and 84 which are each attached to end 81 on one side (e.g. a distal end) of insert 80 and which are each attached to end 82 on the other side (e.g. a proximal end) of insert 80. An open, hollow inner portion is contained within the space defined by the two coils 83 and 84. This open, hollow inner portion may optionally include a tissue ingrowth agent (e.g. polyester fibers) and it may further optionally include an inner member (e.g. a coil, not shown, which resembles coil 76) which is surrounded by the two coils 83 and 84. The insert 80 may be formed from the same materials as insert 70 and may be deployed in the same manner as insert 70. The insert 80 may be designed so that a compressive force on one end of the insert 80 causes the other end to expand. This will tend to provide an anchoring force against the wall of a fallopian tube at least at one point of the insert 80.

The inserts 70 or 70A or 80 may be used with many of the various embodiments described herein and with some of the catheter designs described in the above noted patents. For example, it will be appreciated that the insert 70 is particularly applicable to use in the delivery systems shown in FIGS. 2 and 3 in which the insert 70 is used as the inserts 31 and 33 in the case of FIG. 2 or as the inserts 55 and 56 in the case of FIG. 3.

Figure 6A:
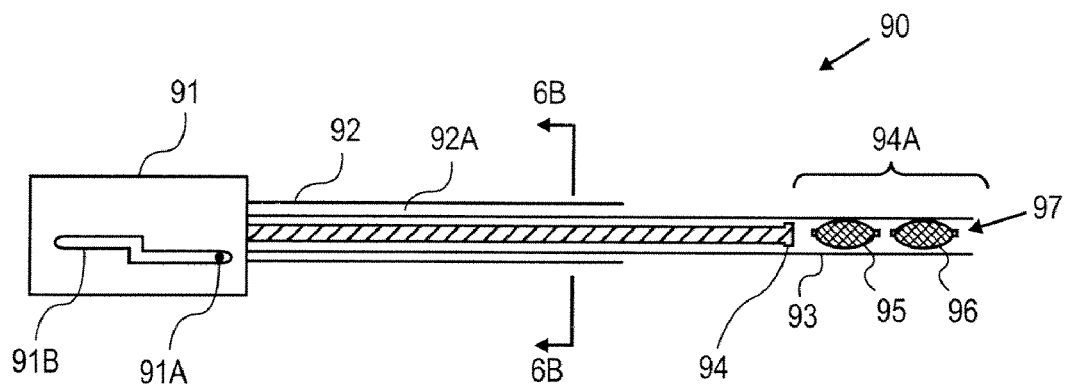
FIG. 6A is a cutaway side view of a delivery system 90 having a proximal control 91 and having two inserts serially disposed in a lumen of the delivery system.
Figure 6B:
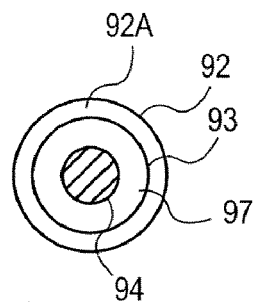
FIG. 6B is a cross-sectional view of the delivery system of FIG. 6A, wherein the view of FIG. 6B is taken at the line 6B-6B as shown in FIG. 6A.
Figure 6C:
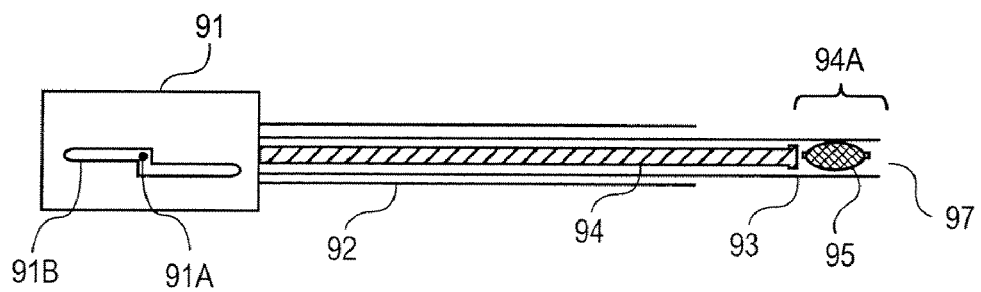
FIG. 6C is a cutaway side view of the delivery system of FIG. 6A after one of the inserts has been deployed from the delivery system.

FIGS. 6A, 6B and 6C show one particular delivery system which uses inserts which resemble the insert shown in FIG. 5A. In the delivery system shown in FIG. 6A, the delivery system 90 includes a proximal control 91 and a tube 92 which is coupled to the proximal control 91. Tube 92 may, in certain embodiments, be a stainless steel hypotube which is small in diameter and has thin walls. In certain alternative embodiments, the tube 92 may be omitted. It will be appreciated that while the delivery systems shown in FIGS. 2, 3, and 6 and elsewhere are shown in a straight, unbent configuration, these delivery systems will typically be flexible, allowing at least a portion of the longitudinal extent of the delivery system to bend in order to fit within tortuous body lumens such as the uterus and the fallopian tube (see, for example, FIG. 19). The delivery system 90 includes a distal portion which includes two inserts 95 and 96 disposed within a lumen 97 of a delivery sheath 93. The inserts 95 and 96 are in the distal portion 94A along with the end of a rod 94 which in this case is a stationary rod. The delivery sheath 93 fits within the lumen 92A of the tube 92. The hypotube is stationary relative to the proximal control while the delivery sheath is retractable relative to the proximal control. Further, the rod 94 is stationary relative to the proximal control, and the delivery sheath 93 is retracted in a proximal direction by moving the knob 91A in a proximal direction along the slot 91B. The slot 91B includes two longitudinal portions which are parallel with the longitudinal dimension or direction of the delivery system 90 and a transverse portion which is perpendicular to this direction and connects the two portions of the slot 91B. This transverse portion serves the same function as described above with respect to the slot 21B in that it allows the physician to control the selective and singular deployment of each insert. As the physician moves the knob 91A in the position shown in FIG. 6A to the position shown in FIG. 6C, the delivery sheath 93 is retracted, allowing the first insert to be exposed and to be deployed outside of the delivery sheath 93. At this point, the insert may begin to expand once it is released from the delivery sheath to become lodged into a portion of the fallopian tube. When the physician reaches the midpoint of the slot as shown in FIG. 6C, the first insert will have been deployed and then the physician may move the delivery system from the entrance of the first fallopian tube to the entrance of the second fallopian tube in order to deploy the second insert. At the point of use as shown in FIG. 6C, the distal portion 94A represents a retracted distal portion which still retains the second insert but which has released the first insert. FIG. 6B shows a cross-sectional view of the catheter at lines 6B-6B of FIG. 6A.

The embodiments shown in FIGS. 6A-6C and FIG. 2 assume that there is no mechanical connection between the two inserts. Such a system in which there is no connection between the two inserts may be used where there is sufficient friction between the insert and the inner wall of the delivery sheath to retain the insert within the delivery sheath but yet not too much resistance or friction which prevents the inserts from being pushed out or having the delivery sheath retracted relative to the stationary rod and inserts. The embodiment shown in FIGS. 7A-7E, on the other hand, may include a mechanical connection (e.g. a screw or interlocking connection) between the two serially disposed inserts within the delivery system 100.

Figure 7A:
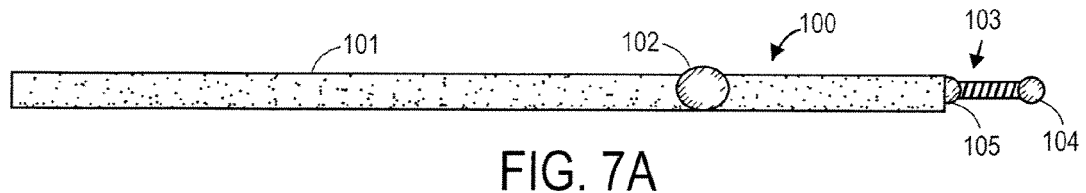
FIG. 7A is a top view of a delivery system 100.
Figure 7B:
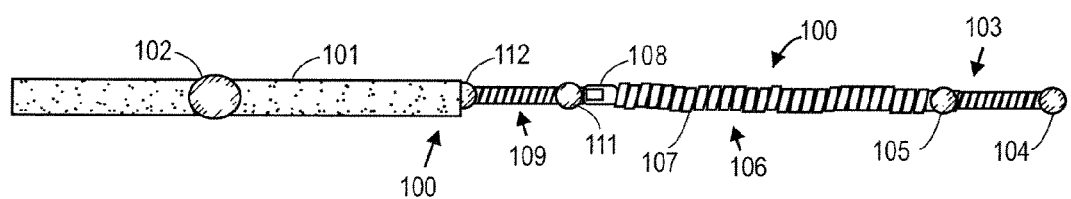
FIG. 7B is a top view of the delivery system 100 after a delivery sheath has been partially retracted.
Figure 7C:
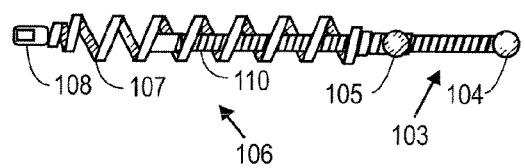
FIG. 7C shows a top view of the first insert 106 after it has been deployed from the delivery system 100.
Figure 7D:
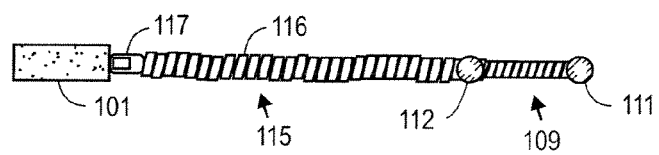
FIG. 7D shows the delivery system 100 after the delivery sheath 101 has been further retracted to reveal the second insert 115.
Figure 7E:
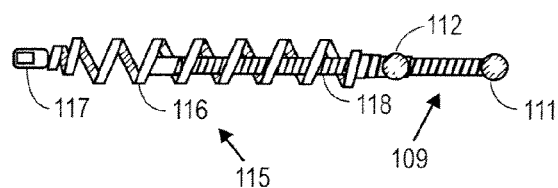
FIG. 7E shows a top view of the second insert 115 after it has been deployed from the delivery system 100.

FIG. 7A shows the delivery system 100 which includes a delivery sheath 101 and a marker 102 disposed on the delivery system 100. The marker 102 may be one or more of the various types of conventional markers such as an optically visible marker (e.g. a marker which is colored to distinguish from its surroundings) which is visible during a hysteroscopy by visible light and a camera or a radiopaque marker or an ultrasound marker (which is visible in an ultrasound image) or other known markers which allow the user of the system 100 to guide and place the distal end of the system at a proper deployment position. A distal portion 103 of a first insert includes a tip 104 and an attachment mechanism 105 (which may be a solder bond, for example) which is part of a first insert 106 (not shown in FIG. 7A). FIG. 7B shows the delivery system 100 after the delivery sheath 101 has been retracted (or alternatively, both inserts have been pushed relative to the delivery sheath) such that the first insert 106 is fully viewable and a portion (the distal portion 109) of the second insert 115 is visible in the view of FIG. 7B. The first insert includes an outer coil 107 which is attached at attachment 105 to an inner coil 110 shown in FIG. 7C. The inner coil may extend from the tip 104 in a proximal direction toward an end piece 108 which is attached to the outer coil 107. The outer coil 107 is thus coupled to the inner coil at attachment 105 and coupled to the end piece 108 as shown in FIG. 7C. The end piece 108 is adjacent to and abuts the tip 111. The tip 111 may include a pin or other interface designed to mate with a receptor or other interface on the end piece 108 to thereby couple the first insert 106 to the second insert 115. In one exemplary embodiment, the two interface elements on the tip 111 and the end piece 108 may resemble a screw and a nut which more securely secures the two inserts to each other. The two inserts can be released by unscrewing the second insert from the first insert after the first insert has been implanted. FIG. 7D shows the second insert after the delivery sheath has been moved to a position past the end piece 117 to allow the deployment and release of the second insert 115 which includes an outer coil 116 which is attached to the inner coil 118 at the attachment 112 of the second insert 115. The inner coil 118 may extend from the tip 111 through the attachment 112 and proximally towards the end piece 117 which is coupled to the proximal end of the outer coil 116. The inserts shown in FIGS. 7A-7E resemble the inserts used within the Essure device from Conceptus, Inc. of San Carlos, Calif., in that there is an outer coil which may be formed from a superelastic or resilient member and an inner coil which is coupled to the outer coil. The outer coil is designed to radially expand to engage the walls of a portion of the fallopian tube to thereby engage those walls and hold the device within the fallopian tube. It will be appreciated that the inserts shown in FIGS. 7A-7E may include a tissue ingrowth agent such as a polyester fiber or other types of agents designed to cause tissue ingrowth to functionally occlude the fallopian tube. Functional occlusion of the fallopian tube is described, for example, in U.S. Pat. No. 6,526,979 which has been incorporated herein by reference.

Figure 7F:
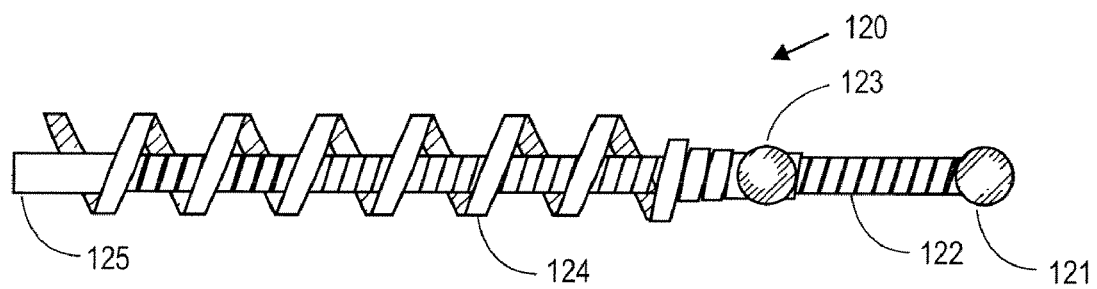
FIG. 7F shows in a top view an alternative embodiment of an insert which may be used in certain embodiments of the invention.

FIG. 7F shows another exemplary embodiment of an insert which includes two types of coils, an inner coil 122 and an outer coil 124 which is coupled to the inner coil by an attachment 123. This insert 120 also includes a tip 121 which is also the distal end of the inner coil 122. The inner coil 122 may run through the interior of the attachment 123 which secures the outer coil 124 to the inner coil 122. The inner coil 122 ends at its proximal end with an end piece 125. It can be seen from FIG. 7F that the outer coil 124 is not coupled to the end piece or to any other piece which is aligned with a longitudinal axis of the inner coil 122. The outer coil 124 may be radially expandable upon deployment such that it expands from a first diameter to a second diameter which is larger than the first diameter. The insert 120 may be used in place of the inserts shown in FIGS. 7A-7E such that two inserts of the type shown in FIG. 7F may be serially disposed within a delivery system, which is similar to the configuration shown in FIG. 6A. Alternatively, the insert 120 may be used in a delivery system such as that shown in FIG. 3 where a single insert is disposed within each of the delivery lumens of such a delivery system.

Figure 8A:
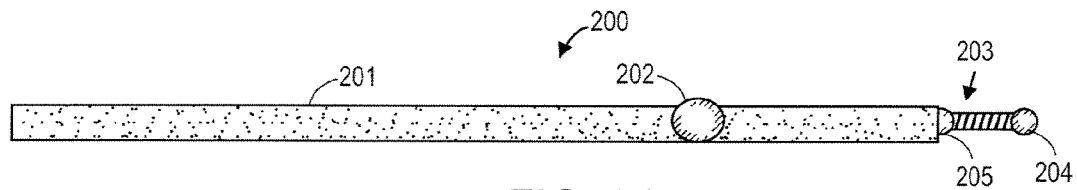
FIG. 8A is a top view of a delivery system 200 which includes two serially loaded inserts.
Figure 8B:
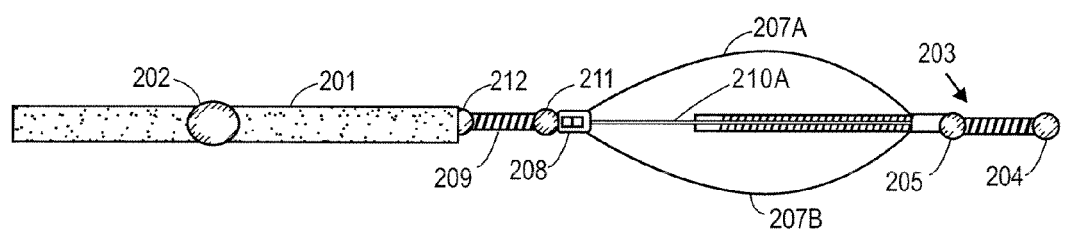
FIG. 8B shows the delivery system 200 after the delivery sheath 201 has been retracted to reveal one of the two inserts.
Figure 8C:
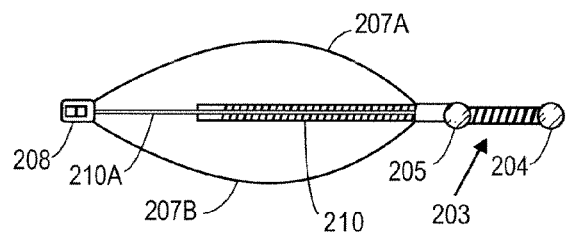
FIG. 8C shows a top view of the first insert shown in FIG. 8B after the insert has been deployed from the delivery system 200.

FIGS. 8A-8D show another embodiment of a delivery system which includes two serially disposed inserts within a delivery system. In this particular embodiment, each of the inserts includes a wing or members which resiliently expand outwardly from a core in order to anchor the insert within the fallopian tube. Normally, these members radially expand outwardly, although other implementations may use different types of expansion. The two inserts are serially arranged in the lumen of a delivery sheath 201 of the delivery system 200. The delivery system 200 includes an imaging marker 202 which may be used to find the position of a portion of the delivery system relative to a fallopian tube in an imaging system such as an optical hysteroscope or ultrasound or other types of conventional imaging systems. The distal portion 203 of the first insert is shown extending beyond the end of the delivery sheath 201 such that the tip 204 (which may be an atraumatic tip) and the attachment 205 are shown in the view of FIG. 8A. In FIG. 8B, all of the first insert is shown and the distal portion 209 of the second insert is shown along with the tip 211 and the attachment 212 of the second insert. The first insert also includes an inner frame 210A which is coupled to a core 210 as shown in FIG. 8C. The attachment 205 couples the core 210 and the top and bottom members 207A and 207B to the distal portion 203 and the tip 204. The inner frame 210A is coupled to an end piece 208 which is coupled to the proximal ends of the top and bottom members 207A and 207B. The distal ends of the members 207A and 207B are coupled to the attachment 205 to secure these members onto the insert. The top and bottom members 207A and 207B, as well as the top and bottom members 216A and 216B, are resilient and expandable from the position shown in FIG. 8B to the positions shown in FIGS. 8C and 8D. FIG. 8C shows the first insert after it has been deployed from the delivery system 200. A delivery wire may be used to help deliver the first and second inserts. This delivery wire may fit within a lumen of the delivery sheath 201 and may press against the proximal end of the second insert. The delivery wire may include a tapered portion at its distal end (e.g. the last 6 cm or more of the distal end may be tapered); this tapering may improve the ability to position the inserts into the fallopian tubes.

Figure 8D:
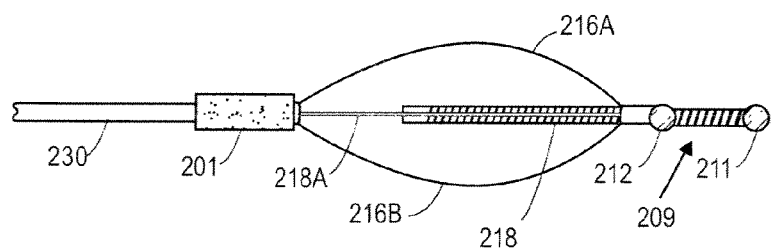
FIG. 8D shows a top view of the delivery system 200 after the delivery sheath has been retracted to reveal the second insert contained within the delivery system 200.

FIG. 8D shows the second insert before it has been deployed while it is still attached to the delivery sheath 201. It can be seen that after the delivery sheath 201 has been retracted to a position near the end piece 208, that the top and bottom members 216A and 216B have expanded radially away from the core 218 and away from the inner frame 218A. These members are attached at their proximal ends to the end piece of the second insert and they are attached at their distal ends to the attachment 212 which is near the distal portion 209 of the second insert. An example of a delivery wire, shown as delivery wire 230, is depicted in FIG. 8D. While FIGS. 8B-8D show an embodiment with two expanding members, it will be appreciated that each insert may have more than two expanding members; for example, each insert may have three or four expanding members (or even more) which are evenly (or not evenly) arranged around the insert. Alternatively, each insert may have only a single expanding member. These expanding members are normally retained in a contracted state while they are being delivered by a delivery system, such as a delivery catheter. As the delivery system deploys or releases the insert, the expanding members expand from the controlled state to the expanded state, thereby engaging the inner wall of a portion of the fallopian tube to tend to anchor the insert within the tube.

Figure 9A:
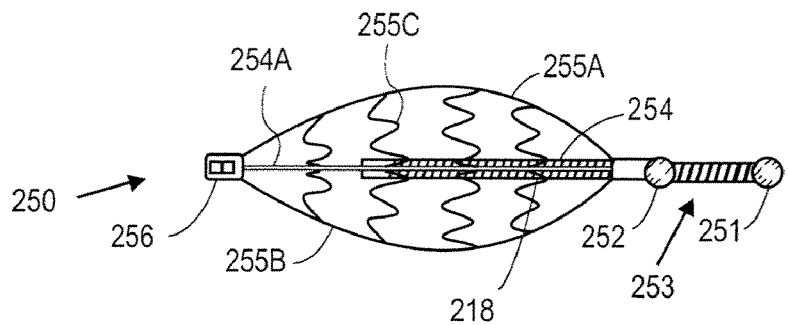
FIGS. 9A, 9B, 9C, and 9D show four alternative inserts which may be used in various embodiments described herein.

FIGS. 9A, 9B, 9C, 9D, and 9E show alternative embodiments of inserts which are similar to the inserts shown in FIGS. 8A-8D. While FIGS. 9A-9E show embodiments with two expanding members, it will be appreciated that each insert may have more than two expanding members (or more than three expanding members in the case of the embodiment of FIG. 9F). For example, each insert may have three or four (or even more) expanding members which are evenly (or not evenly) arranged around the insert. Alternatively, each insert may have only a single expanding member. These expanding members are normally retained in a contracted state while they are being delivered by a delivery system, such as a delivery catheter. As the delivery system deploys or releases the insert, the expanding members expand from the contracted state to the expanded state, thereby engaging the inner wall of a portion of the fallopian tube to tend to anchor the insert within the fallopian tube. The insert 250 of FIG. 9A includes a tip 251 near the distal portion 253 and also includes an attachment 252 which couples the distal end of top and bottom members 255A and 255B to the insert 250. The proximal ends of these members are coupled to end piece 256 which is also coupled to an inner frame 254A which is coupled to the core 254. An inner mesh 255C is coupled to and extends from each of the members to the inner core 254 and to the inner frame 254A as shown in FIG. 9A. The inner mesh may be formed from the same material as the top and bottom members or may be formed from a tissue ingrowth agent.

Figure 9B:
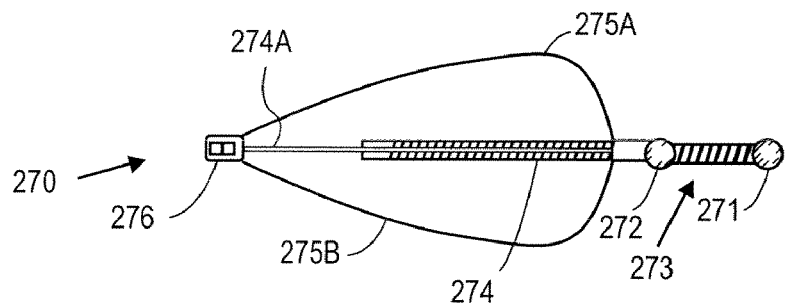

FIG. 9B shows an insert 270 which includes a tip 271 at a distal portion 273 and an attachment 272 which attaches the top and bottom members 275A and 275B to the core 274. The core 274 is attached to an inner frame 274A which is in turn attached to an end piece 276. The proximal ends of the top and bottom members 275A and 275B are attached to the end piece 276 as shown in FIG. 9B. The top and bottom members 275A and 275B may be formed from a material such as a superelastic or shape memory material which radially expands from a contracted state to an enlarged state similar to the manner shown in FIGS. 8A, 8B and 8C. This is also true of the top member 255A and the bottom member 255B shown in FIG. 9A, as well as the other top and bottom members shown in FIGS. 9C, 9D, and 9E.

Figure 9C:
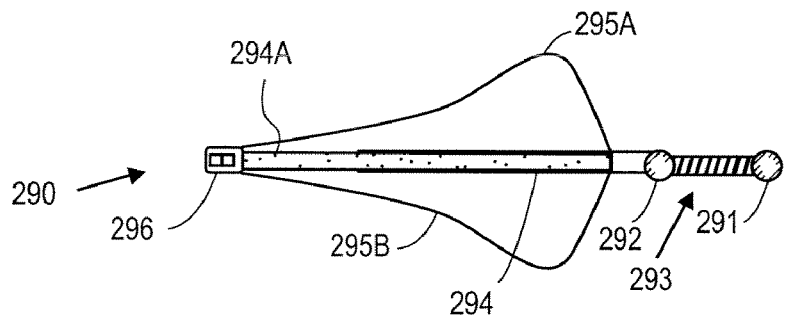

FIG. 9C shows an insert 290 which includes a tip 291 near a distal portion 293 which in turn coupled to an attachment 292 which attaches the top and bottom members 295A and 295B to the core 294 as shown in FIG. 9C. An inner frame 294A which is coupled to the core 294 is coupled at its proximal end to an end piece 296 which in turn is coupled to the proximal ends of the top and bottom members 295A and 295B.

Figure 9D:
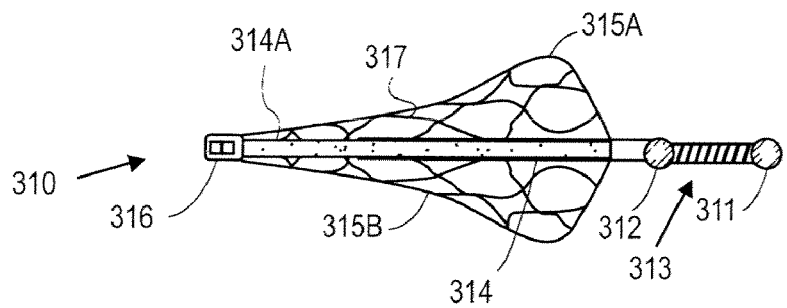

FIG. 9D shows an insert 310 which includes a tip 311 near a distal portion 313. An attachment 312 is coupled to the distal portion 313 and is also coupled to the distal ends of the top and bottom members 315A and 315B. A core 314 is also coupled to the attachment 310, and an inner frame 314A is coupled to the core 314. The proximal portion of the inner frame 314A is coupled to an end piece 316. The end piece 316 is coupled to a proximal end of each of the top and bottom members 315A and 315B. An inner mesh 317, which is similar to the mesh 255C of FIG. 9A, is coupled between the top and bottom members and the core 314 and the inner frame 314A. The inner frame 314A may be the same component as the distal portion 313.

Figure 9E:
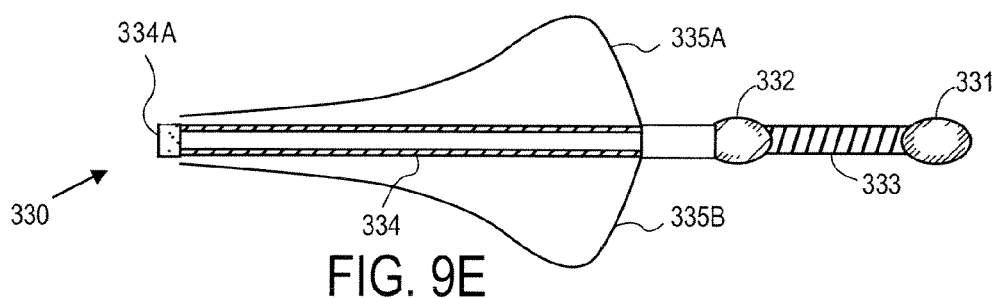
FIG. 9E shows a top view of an insert according to another alternative embodiment which may be used with various delivery systems described herein.
Figure 9F:
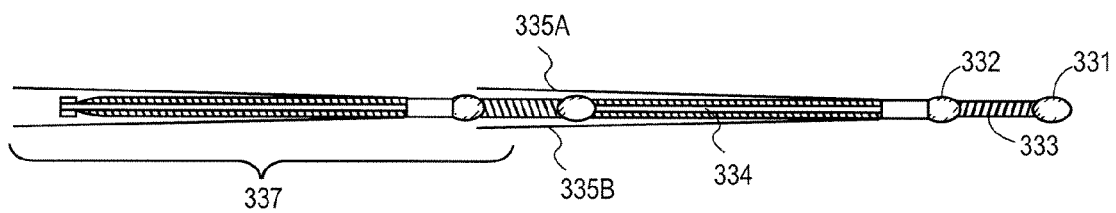
FIG. 9F shows an exemplary embodiment in which two inserts of the type shown in FIG. 9E are serially arranged so they may be deployed from a single lumen of a delivery system.

FIG. 9E shows an alternative embodiment of another insert in which the top and bottom members are secured only to the attachment 332 and not to the end piece 334A which is at the proximal end of the core 334. The insert 330 of FIG. 9E also includes a tip 331 which is coupled to a distal portion 333 which is in turn coupled to an attachment 332. The core 334 may, in an alternative embodiment, be the same component as the distal portion 333. The distal ends of the top and bottom members 335A and 335B are coupled to the attachment 332. The designs shown in FIGS. 9A-9E may be formed from multiple pieces which are brought together or may be formed as one piece. FIG. 9F shows a serial arrangement of two of the inserts 330 in their collapsed form. The second insert 337 is coupled to the first insert at the proximal end of the core 334 of the first insert.

Figure 10A:
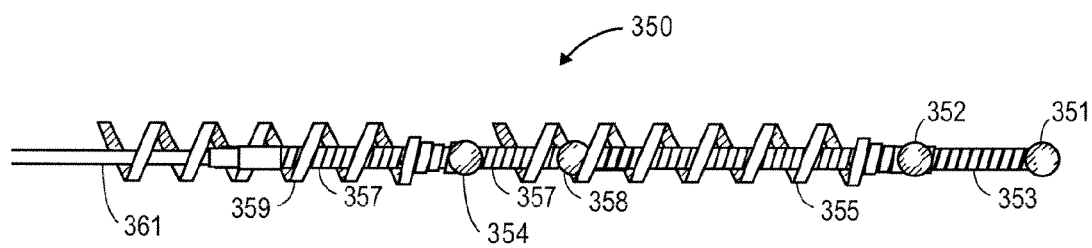
FIG. 10A shows an alternative embodiment of two inserts serially disposed for loading into a delivery system.
Figure 10B:
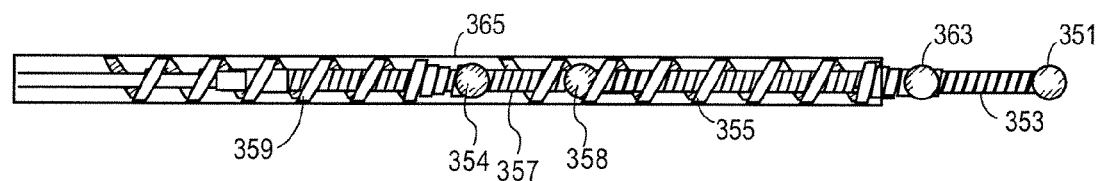
FIG. 10B shows an embodiment in which the two inserts of FIG. 10A are loaded in the delivery sheath which includes a transition attachment near a distal portion of the delivery sheath.

FIGS. 10A and 10B show another alternative embodiment of serially disposed inserts. In this case, the proximal end of the outer coil is not attached to the rest of the insert and is thus similar to the insert shown in FIG. 7F. The dual inserts 350 include a first insert and a second insert attached to a rod 361 which is a form of a delivery wire. The first insert includes a tip 351 which is coupled to an inner coil 353 which extends through and is coupled to an attachment 352. The attachment 352 is coupled to a distal end of the outer coil 355 which may be formed out of a shape memory material or a superelastic material to cause it to expand from a first diameter to a second diameter which is larger than the first diameter. The inner coil 353 extends from the tip 351 to the tip 358 of the second insert. Note how the outer coil 355 overlaps a distal portion of the second insert around the tip 358 and the distal portion of the inner coil 357. The second insert includes the tip 358 which is coupled to the inner coil 357. The inner coil 357 extends through and is coupled to the attachment 354, which attaches the outer coil 359 to the inner coil 357. A distal portion of a delivery system is shown in FIG. 10B which utilizes the dual inserts 350. The tip 351 and a distal portion of the inner coil 353 extends beyond a delivery sheath 365. The outer coil 355 of the first insert and the outer coil 359 of the second insert are fully enclosed within the delivery sheath 365 as shown in FIG. 10B. A transition attachment 363 attaches the outer coil 355 to the inner coil 353. The transition attachment may be shaped in a way to provide a better transition between the inner coil and the sheath, and this transition could be made of a metal or a polymer.

Figure 11A:
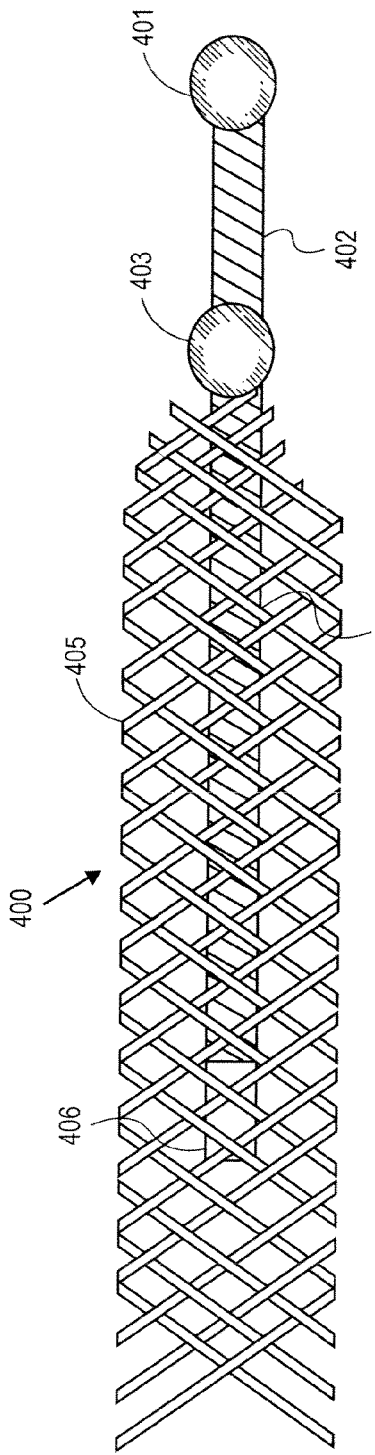
FIG. 11A shows a top view of another alternative insert which may be used in various embodiments described herein.
Figure 11B:
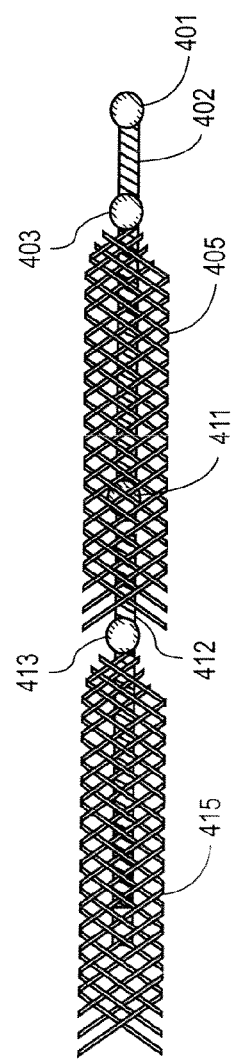
FIG. 11B shows an implementation of two inserts arranged serially, where each insert is similar to the insert shown in FIG. 11A.
Figure 11C:
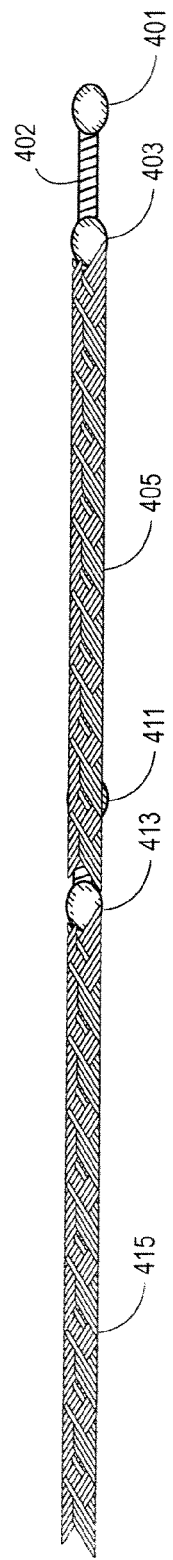
FIG. 11C shows a top view of two serially disposed inserts of the type shown in FIG. 11B where the inserts are in a contracted state in FIG. 11C, and are in an expanded state in FIG. 11B.

FIGS. 11A, 11B, and 11C show another embodiment of an insert which may be used in a delivery system in which two inserts are disposed in a serial fashion within a lumen of the delivery system such as a delivery catheter. In this particular embodiment, the outer member 405 resembles a braided stentlike structure which surrounds an inner coil 402. The outer member 405 is coupled to the inner coil by an attachment 403 which is coupled to the inner coil 402. The distal end of the insert 400 includes a tip 401 which is coupled to the inner coil 402. The tip 401 may be an atraumatic tip which is soft or is otherwise designed to reduce damage to the tissues which may be impacted with the tip when the insert is being delivered. It will be appreciated that the other tips described herein may also be atraumatic tips. The inner coil 402 ends in an end piece 406 as shown in the example of FIG. 11A which shows the outer member 405 in an expanded state. FIG. 11B shows two such inserts, each with their outer member in an expanded state, where the inserts are serially arranged. The second insert includes the tip 411 which is coupled to an inner coil 412 which is in turn coupled to an attachment 413. The attachment 413 attaches the outer member 415 to the inner coil 412. This attachment may be a soldered connection or a glued connection. FIG. 11C shows the dual inserts of FIG. 11B with the outer members retracted in their contracted states rather than the expanded states shown in FIG. 11B.

FIGS. 12A-12H generally relate to an aspect of the inventions in which at least a portion of the insert is partially molded or extruded out of a polymer. This typically will allow the insert to be fabricated in a manner which is cheaper (or less complicated) than inserts made entirely out of metal, such as two or more coils which are attached to each other. Further, the inserts themselves may be easier to manufacture and hence less expensive than inserts which are formed from two or more coils of metal. The inserts shown in FIGS. 12A-12H may be formed entirely from a polymer material or substantially (e.g. the composition of the entire insert is at least 65% polymer by weight, with the remainder being metal) from a polymer material. The polymer may be a non-biodegradable polymer material which remains permanently within the fallopian tube and these inserts may include tissue ingrowth agents which encourage or cause the growth of tissue into and through at least a portion of the insert. Thus, the inserts, which may include a non-biodegradable polymer, may include openings which allow tissue ingrowth into the openings of the inserts, and the induced tissue ingrowth may be completely through or substantially completely through these openings in order to provide a functional occlusion. The polymer content may range from as low as about 2% (by weight) to as high as about 100% (by weight). The insert may also (optionally) be toxic to sperm or to reproductive cells or progeny of such cells. These inserts (e.g. the inserts shown in FIGS. 12A-12H) are pre-formed (e.g. manufactured into their desired shapes) prior to insertion into a fallopian tube. These inserts may include a hydrophobic surface (e.g. at least a portion of the outer surface which faces the walls of the fallopian tube is hydrophobic); this will tend to improve the retention of the insert within the fallopian tube.

The polymer material or materials used in these inserts (e.g. the inserts of FIGS. 12A-12H) may include polyurethane, a silicone urethane copolymer, a polyester, a polyethylene, a polycarbonate, a silicon, a PTFE (such as an ePTFE), polypropylene, ABS, a silicone and collagen ("collimer") combination, acrylic, nylon, Pebax, FEP, Teflon or PVP. The insert may also include one or more moldable metals (which is co-extruded with an organic polymer or is insert molded), and the metals may include silver, nickel, copper, a beryllium copper alloy or material, platinum or a stainless steel material.

Figure 12A:
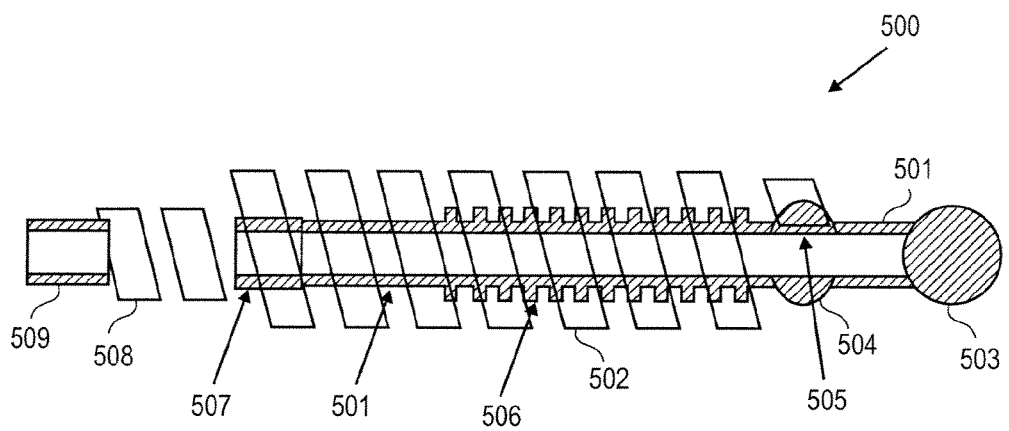
FIG. 12A shows a side view of an example of an insert according to certain embodiments of the present invention, wherein a portion of the inner member is shown in a partial cutaway view.

FIG. 12A shows an embodiment of an insert 500 which is formed in part from a polymer and in part from a metal coil which may be similar to the outer coil of the inserts shown in FIGS. 7A-7E. The insert 500 includes an inner member which may be molded or extruded from a polymer. The molding operation may be an injection molding operation with materials which are suitable for the injection molding operation and this operation may be used to produce an injection molded polymeric inner member. Urethanes and silicone containing materials may be suitable for an outer coil shown in an alternative embodiment of FIG. 12B in which the entire insert is formed out of a polymer.

In the case of the embodiment shown in FIG. 12A, the inner member 501 may be formed out of a polymer, such as a plastic through an injection molding operation or an extrusion operation. This molding operation may be an insert molding operation wherein a portion of the metal coil 502 which forms the outer coil is placed into the mold such that the distal end 505 of the outer coil is embedded within the polymer material in the mold during the molding operation to thereby secure the outer coil to the inner member 501. This securement occurs at the attachment 504. The inner member 501 includes a tip 503 which may be atraumatic and which is designed to be arranged at a distal end of the insert 500. The inner member 501 is designed with teeth 506 formed by the die or mold; these teeth are designed to, in one embodiment, engage a meshlike material such as polyester fibers or other fibers or furs which are designed to promote a tissue ingrowth and which are one embodiment of a tissue ingrowth agent. This is shown in FIG. 12C in which the tissue ingrowth agent 541 is secured by the teeth 506 such that the tissue ingrowth agent is disposed between the outer coil 502 and the inner member 501. The inner member 501 has a proximal end 507. The insert 500 also includes another molded piece (formed from a polymer material) which is the end piece 509 which is attached to a proximal end of the outer coil. Thus the outer coil has a distal end which is coupled to the attachment 504 of the inner member 501 and has a proximal end which is attached to the end piece 509. Both attachments may occur through an insert molding operation in which a portion of the outer coil (which may be metal) is placed into the die which is used to form both the inner member 501 and the end piece 509 in the same or separate molding operation; alternatively, two separate dies (one for the inner member 501 and the other for the end piece 509) may be used. It will also be appreciated that the end piece 509 may be formed from a metal and thus it may be an extension of the outer coil 502.

Figure 12B:
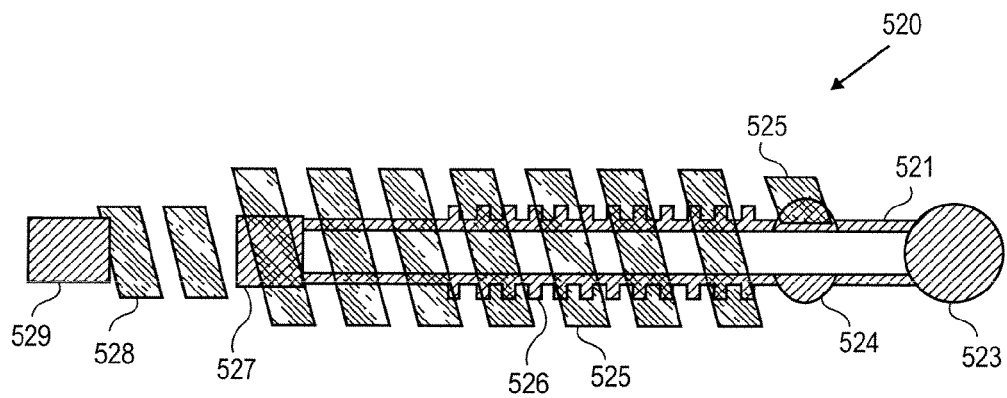
FIG. 12B shows another embodiment of an insert which may be used in embodiments of the invention; the view of FIG. 12B is a side view with a cross-sectional view of an inner member.
Figure 12C:
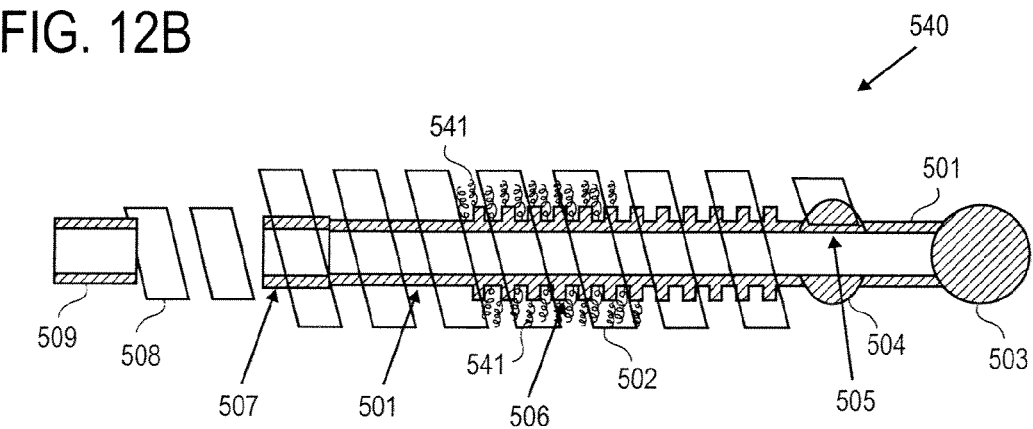
FIG. 12C shows another exemplary embodiment of an insert according to certain embodiments of the invention; the view of FIG. 12C is a side view with a partial cutaway side view of the inner member.

FIG. 12B shows an alternative embodiment in which the insert 520 is formed completely out of a polymer material through a molding operation or an extrusion operation or some other fabrication method. It will be appreciated that the parts may be separately fabricated and then assembled with an adhesive (or the parts may be crimped together or tied with fiber or attached together in other ways). The insert 520 includes an inner member 521 which includes a tip 523 located at a distal end of the inner member and an attachment 524 which attaches the inner member to the outer coil 525 which is also formed out of a polymer. Teeth 526 are disposed on the outer surface of the inner member and may be used to engage a tissue ingrowth agent, such as that shown in FIG. 12C. The proximal end 527 of the inner member is spaced apart from an end piece 529 which is coupled to a proximal end 528 of the outer coil. The outer coil may be made from urethanes or silicone containing materials. Thus, for example, the outer coil may be made from polyurethanes such as polycarbonate uretheanes and polyether urethanes. The inner member may be fabricated from polyester or polyethylene or polycarbonate.

FIG. 12D shows a delivery system 570 which includes an insert which is similar to the insert shown in FIG. 12A. The insert of FIG. 12D includes an inner member 577 which is formed out of a polymer and an outer coil 578 which would be formed out of a metal which is insert molded into the die or mold used to form the inner member 577. The inner member includes a tip 579 at its distal end. Outer coil 570 is coupled to an attachment at the distal end of coil 578 and is coupled at a proximal portion 576 to an end piece 581. The end piece 581 and the inner member 577 may be fabricated out of a polymer, such as a polyurethane (e.g. polycarbonate or urethane) or a silicone urethane copolymer, or a polyester, or a polyethylene, or a polycarbonate. The outer coil member may be fabricated out of nitinol and be superelastic or otherwise radially expandable into a shape which engages the walls of the fallopian tube. The end piece 581 is designed to be pushed by the end face 575 of the rod 572 during the process of deploying the insert from the lumen 574. The deployment process may involve either retracting the delivery sheath 573 relative to a stationary tube 571 or pushing the rod 572 relative to a stationary delivery sheath 573 to thereby push the insert out of the lumen 574.

FIG. 12E shows an exemplary embodiment in which a partially molded or extruded insert or a fully molded or extruded insert 520 is being deployed from the delivery system 590 by retracting the delivery sheath 592 relative to a stationary tube 591 and relative to a stationary rod 593. The end face 594 of the rod mates against the end piece of the insert 520 and the delivery sheath 592 is retracted to a point causing the insert to be released from the delivery system 590.

Figure 12F:
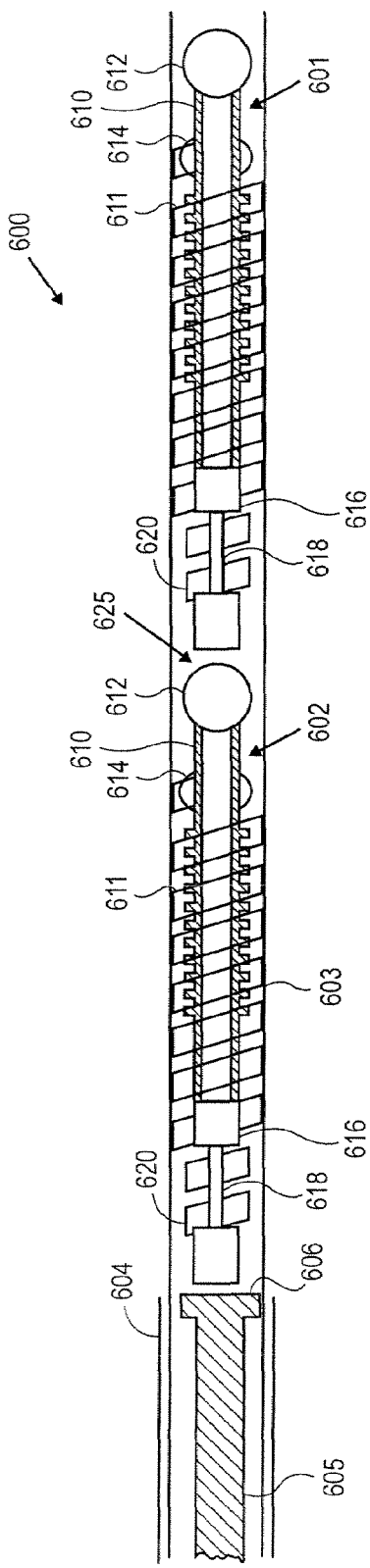
FIG. 12F shows a cutaway side view of a delivery system having two inserts serially loaded into the delivery system.
Figure 12G:
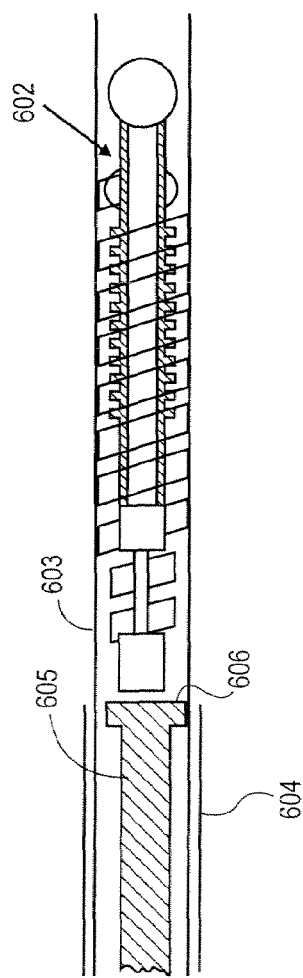
FIG. 12G shows the delivery system of FIG. 12F after the delivery sheath has been partially retracted to deploy the first insert.

FIG. 12F shows an implementation of a delivery system delivery system which includes two molded inserts 601 and 602 serially disposed within the lumen of a delivery sheath 603. A rod 605 is also disposed within the same lumen, and in this embodiment, the rod is a stationary rod relative to a stationary tube 604 (which may be a hypotube) while the delivery sheath 603 is moveable such that it can be retracted to release the first insert and then the second insert in a serial operation. Each insert 601 and 602 includes an inner member 610 and an outer coil 611 which is coupled to the inner member at an attachment 614. Each insert further includes a tip 612 and a proximal end 616 of the inner member and a connecting rod 618 which connects the proximal end 616 to an end piece which is attached to the proximal end 620 of the outer coil. There may be a space 625 between the first and second insert 601 and 602 or there may be an optional separator which is a biodegradable material which provides some separation between the two inserts. This separation may be useful in order to assure that only one insert is disposed and deployed into one fallopian tube at a time. Since the optional separator is biodegradable, deploying a separator into a fallopian tube is not a harmful operation and will tend to prevent the deployment of a second insert in the same fallopian tube. The end piece of the second insert abuts the end face 606 of the rod 605 during the deployment operation. FIG. 12G shows the delivery system 600 after the first insert has been deployed by retracting the delivery sheath 603, but the second insert 602 still remains within the delivery sheath and has yet to be deployed from the delivery system.

Figure 12H:
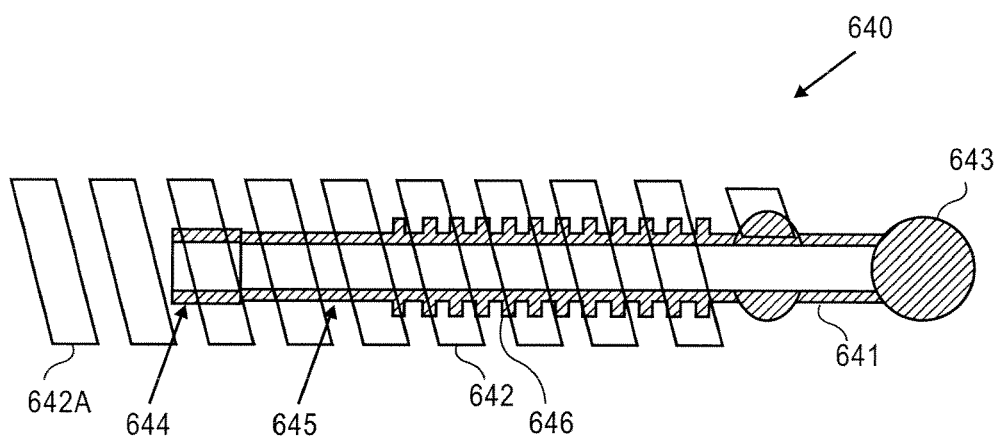
FIG. 12H shows an alternative embodiment of an insert, wherein the view of FIG. 12H is a side view with a partial cross-section of the inner member.

FIG. 12H shows yet another embodiment of an insert which includes a molded or extruded polymer material. In this case, the insert 640 does not include an end piece which is attached to the proximal end 642A of the outer coil 642. This insert resembles the inserts shown in FIG. 10A or the insert shown in FIG. 7F in that the proximal end of the outer coil is allowed to stand freely relative to any other structure of the insert. The distal end of the outer coil 642 is coupled to an attachment which is at the distal end 641 of the insert. A tip 643 is at the far distal end of the insert. The inner member 645 is attached to the outer coil 642 at the attachment point, and the inner member also includes teeth 646 which may be used to attach a tissue ingrowth agent to the insert. The proximal end of the insert 640 includes an end piece 644 which is not attached to the outer coil 642.

The embodiment shown in FIG. 12H may be one in which the outer coil is a metal which is inserted into a mold during an insert molding operation such that the metal becomes attached to the polymer (e.g. plastic) material which is used to form the inner member. This allows the metal coil to be expandable or resilient or to have a shape memory (e.g. memorized shape) or to be superelastic to thereby radially expand or otherwise expand to fit tightly within a fallopian tube in order to prevent the insert from being pushed out of the fallopian tube. The metal coil, after it radially expands to engage the wall of a fallopian tube, provides an anchoring force which resiliently presses against the wall to resist any expulsion forces applied by the fallopian tube.

It will be appreciated that other methods may be used to fabricate the inserts described herein which are at least partially formed out of a polymer. For example, a liquid silicone casting operation may be used to form at least a portion of an insert out of silicone, and a RAM extrusion process may be used with ePTTE materials to create at least a portion of a polymer based insert.

Figure 13A:
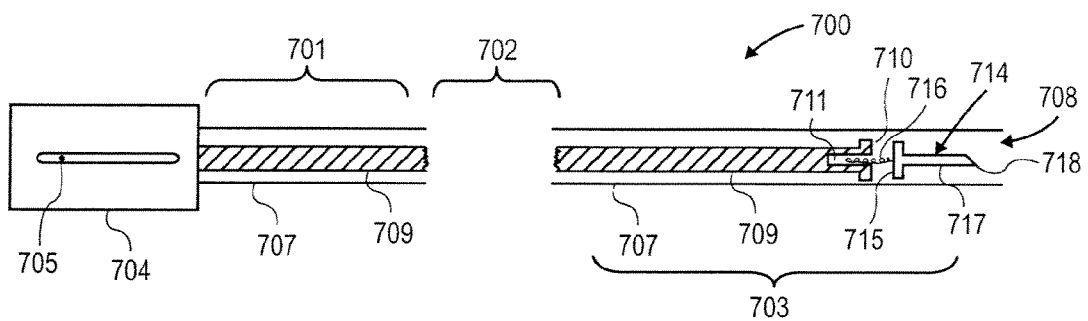
FIG. 13A is a cutaway side view of a delivery system having an insert 714 and a proximal control 704 coupled to the delivery system.

FIGS. 13A, 13B, 13C, 13D, 14A, 14B, 14C, 15, 16A, 16B, 16C, 16D, 17A, 17B, 18A, 18B, 18C, and 18D, and 19 relate to another aspect of the present invention, and these figures show various different embodiments according to this aspect. In the exemplary embodiment of FIG. 13A, a delivery system 700 includes a proximal portion 701, a middle portion 702, and a distal portion 703. A control unit 704 is coupled to the proximal portion, and the control unit includes a knob 705 which is used to move the rod 709 within the lumen 708 to push out the insert 714. The rod 709 is disposed within a delivery sheath 707 which forms the lumen 708 and which contains both the rod and the insert 714. The rod 709 may be pushed relative to the delivery sheath by moving the knob 705 in a distal direction. A groove 711 at the end of the rod provides space for a tissue ingrowth agent 716 which is attached to an end face 715 of the insert 714. The end face 715 is designed to engage the end face 710 of the rod when the rod is pushing the insert 714 out of the lumen 708. The insert further includes a shaft 717 which is attached to the end face 715 and which ends in a distal tip 718 which is typically a sharp tip designed to pierce a portion of the fallopian tube.

Figure 13B:
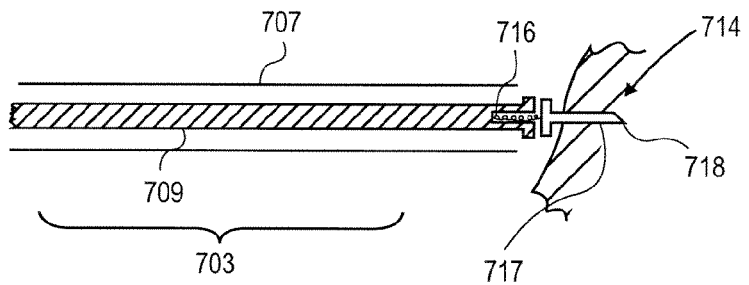
FIG. 13B shows a distal portion of the delivery system 700 as the insert 714 is being deployed.
Figure 13C:
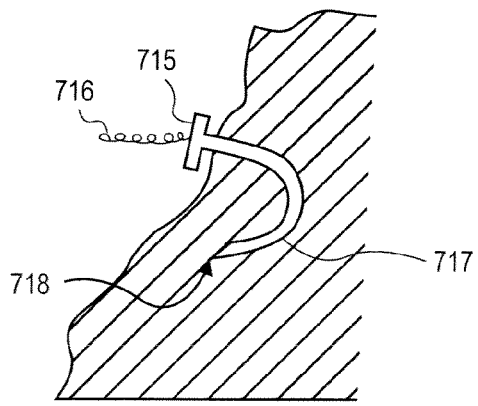
FIG. 13C is a cross-sectional view of the insert 714 after it has been deployed.

FIG. 13B shows an example of how the insert 714 is deployed by pushing the insert into a portion of the fallopian tube. The distal portion 703 of the delivery system 700 is shown near a portion of the tissue of the fallopian tube. The push rod 709 has pushed the insert 714 into the tissue of the fallopian tube. In one embodiment, the shaft 717 has a substantially straight configuration and begins to bend immediately after it has exited the delivery system or after it has entered the tissue of the fallopian tube or soon thereafter. The shaft may be made from a superelastic material or a shape memory material (e.g. nitinol) or a material which is both superelastic and is a shape memory material. The shaft 717 may bend in many different directions including a proximal direction or a distal direction. In certain embodiments, the shaft may begin to bend as soon as the insert begins to be pushed out of the delivery system. The shaft 717 may be kept substantially straight during at least a portion of the deployment process by at least one of several techniques, including the use of at least one straightening member which is retractably disposed within a hollow portion of the shaft 717 and/or the use of a shape memory material that changes from a straight shape to a curved shape after a change in state (e.g. a change in temperature of the material or a change which is induced by the application of an electric current) or after being activated (e.g. activated by directing Radio Frequency energy at the material). In the case of the straightening member, the straightening member is a short, rigidly straight object attached to a delivery wire which is used to control the position of the straightening member relative to the shaft 717. When the straightening member is disposed within the hollow portion of the shaft 717, the shaft 717 is kept substantially straight, and once the straightening member is retracted out of the hollow portion, the shaft forms a curve. FIG. 13C shows a cross-sectional view of the insert 714 after it has been implanted into a portion of the fallopian tube. It can be seen that the shaft has bent from a substantially straight shape to a curved shape, which in this case is a curve that is bent proximally back toward the cervix. The insert may remain substantially buried except for the end face 715 and the tissue ingrowth agent 716. In certain embodiments, the distal tip may reemerge as shown in FIGS. 14B and 14C after being implanted into a portion of the fallopian tube.

Figure 13D:
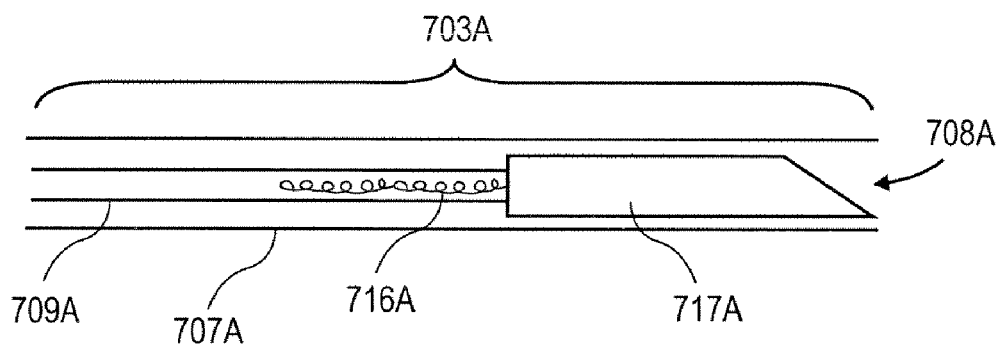
FIG. 13D is a cutaway side view of a distal portion of an alternative embodiment of a delivery system which includes an alternative insert device as shown in FIG. 13D.

FIG. 13D shows another embodiment of an insert which is designed to pierce and bend into a portion of the fallopian tube. This insert has a first configuration which is substantially straight and a second configuration which typically bends (e.g. bends proximally into or distally away) in the tissue of the fallopian tube. The insert includes a shaft 717A which has at its distal end a sharp tip and at a proximal end a tissue ingrowth agent 716A. A hollow tube 709A (which may be a hypotube) is used to push the insert out of the lumen 708A from the distal portion 703A of the delivery system. The tube 709A and the insert are housed within a delivery sheath 707A which forms the lumen 708A. The tissue ingrowth agent 716A is disposed within the hollow portion of the hollow tube 709A. The hollow tube is typically coupled to a control mechanism at a proximal end of the delivery system so that the hollow tube can be used to push (relative to the delivery sheath) the insert out of the lumen to allow it to be deployed into the tissue of a fallopian tube. The tube 709A may, in an alternative embodiment of the system shown in FIG. 13D, be replaced by a solid rod (e.g. a delivery wire) with a hollow space at its distal end; this hollow space is used to hold the tissue ingrowth agent 716A. This solid rod is coupled to a control mechanism, at a proximal end of the delivery system, which is used to control movement of the solid rod so that the insert can be pushed out of the delivery system. The tube 709A may, in yet another alternative embodiment of the system shown in FIG. 13D, be replaced by a coiled spring which can be used to push out the insert which includes the shaft 717A and the tissue ingrowth agent 716A.

Figure 14A:
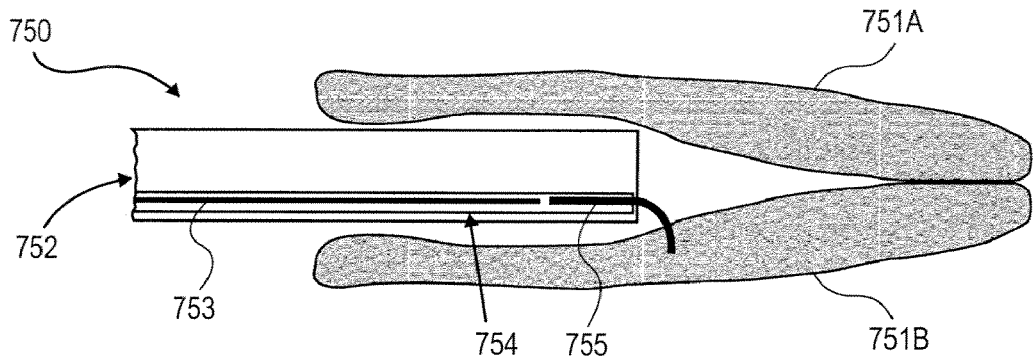
FIG. 14A shows a cross-sectional view of a delivery system which is in the process of deploying an insert into a portion of a fallopian tube.
Figure 14B:
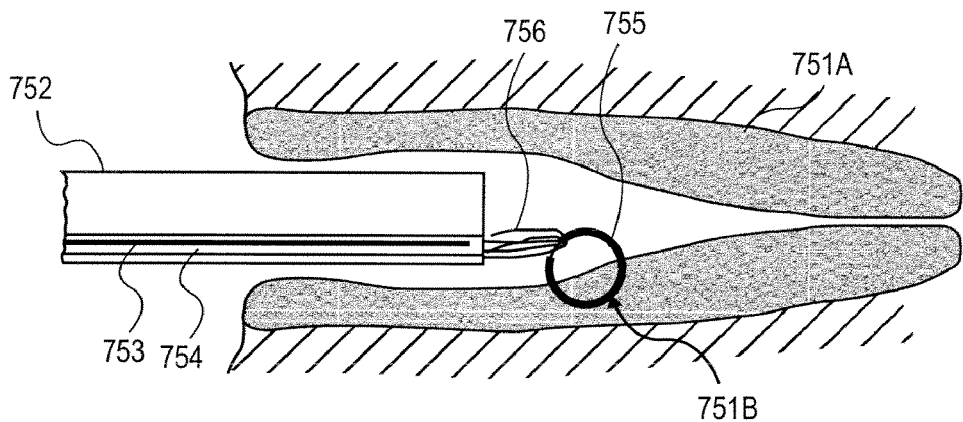
FIG. 14B shows another cross-sectional view of the delivery system of FIG. 14A after the insert has been nearly completely released from the delivery system.
Figure 14C:
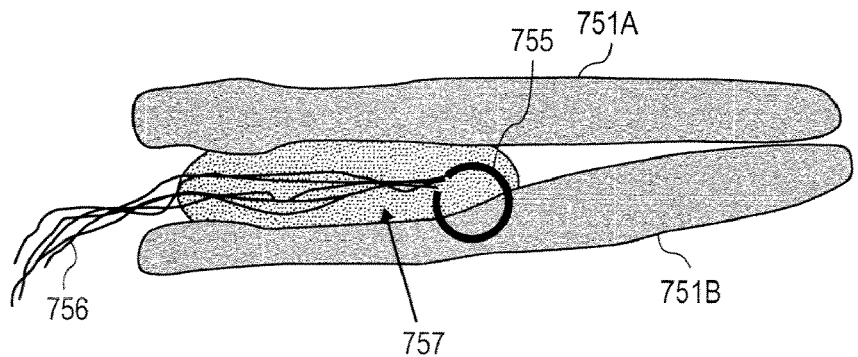
FIG. 14C shows a cross-sectional view of the tissue ingrowth which occurs in the fallopian tube after the insert has been implanted within the fallopian tube for a period of time.
Figures 18A, 18B, 18C:
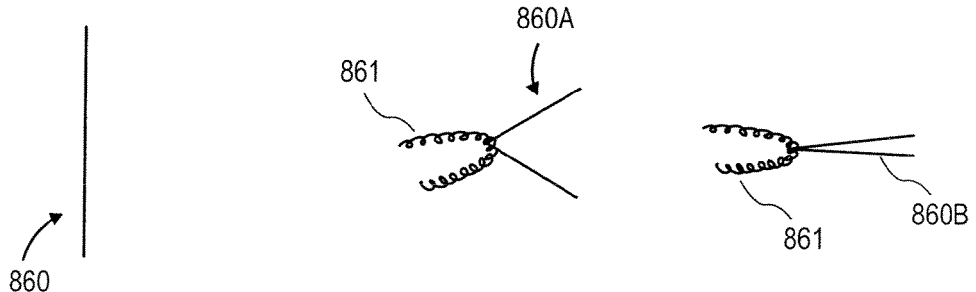
FIG. 18A shows the precursor of an insert in a side view of the insert.
FIG. 18B shows the formation of an insert by the process of bending the shaft shown in FIG. 18A.
FIG. 18C is a side view of the insert after it has been further bent from the configuration shown in FIG. 18B.

FIGS. 14A, 14B, and 14C show another embodiment of an insert which is pushed into and which bends within the tissue of the fallopian tube. In this example, a delivery system 750 includes a delivery shaft 752 which has a lumen 754 in which a hollow tube 753 is disposed. An insert 755 (which may be formed at least in part from a superelastic material or a shape memory material or a material which is both superelastic and is a shape memory material) is also disposed within this lumen 754 and is pushed out of the lumen in the deployment process by pushing the tube 753 in a distal direction to push the insert 755 out of the lumen 754. The insert 755 includes a tissue ingrowth agent (not shown in FIG. 14A but shown in FIG. 14B). The tube 753 may be a hypotube or other type of tube or it may be replaced, in an alternative embodiment, by a solid rod (e.g. a delivery wire) with a hollow space at its distal end; this hollow space may be used to hold the tissue ingrowth agent 755. This solid rod is coupled to a control mechanism, located at a proximal end of the delivery system, which is used to control movement of the solid rod so that the insert can be pushed out of the delivery system. FIG. 14B shows the insert 755 having been substantially pushed out of the delivery system with the tissue ingrowth agent 756 at the proximal end of the insert 755. At this point, the delivery system can be removed so that the tissue ingrowth agent and the insert 755 can remain in the fallopian tube to cause the tissue ingrowth as shown in FIG. 14C, in which the tissue ingrowth 757 has completely blocked, or at least blocked in this view (to provide functional occlusion), the fallopian tube which includes the walls 751A and 751B of the fallopian tube. It will be appreciated that the insert may be made from a shape memory material such as nitinol which is annealed to give the memory shape. It may be formed from a nitinol wire which has a length of approximately 1 mm to about 6 mm. The wire may have a diameter of approximately 5/1000 of an inch and the delivery shaft 752 may have a diameter of approximately 1 mm. In one embodiment, the tissue ingrowth agent may be a polyester or Dacron fiber which is attached to the distal end of the shaft or other types of tissue ingrowth agents which are known in the art. These fibers may, in one exemplary embodiment, be approximately one inch long and have a mass of about 1.5 mg. In other embodiments, these fibers may be from about 2 mm to about 3 cm in length. The length of the shaft may be approximately 3 mm long if the diameter of the loop desired to be created by the insert as shown in FIG. 14B and 14C is about 1 mm. Typically it is desirable to form a loop having a diameter from about 0.5 mm to about 2.0 mm. The tissue ingrowth agent may be applied to the insert device by a number of techniques including using a biocompatible adhesive or melting of the polyester fibers onto a textured implant or tying or sewing each fiber onto the implant or crimping the fibers onto the implant as shown in FIG. 18C.

Figure 15:
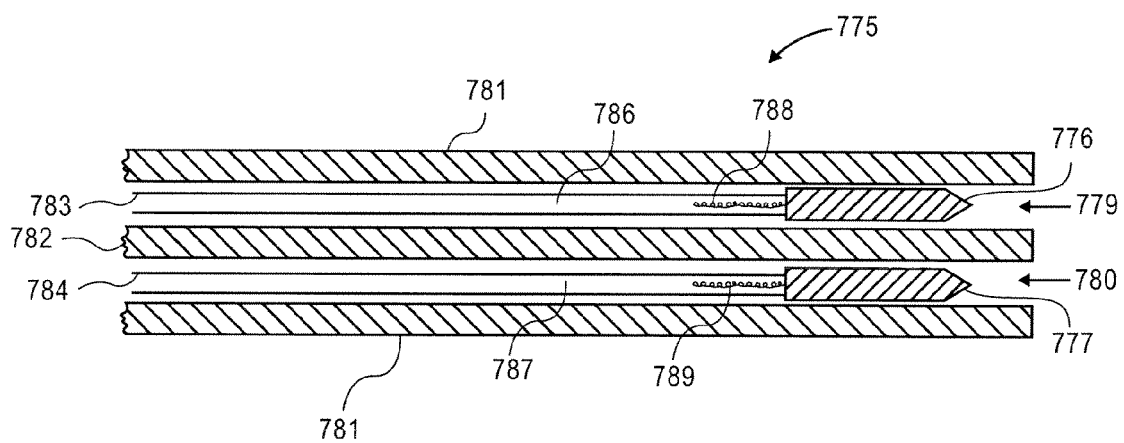
FIG. 15 is a cross-sectional view of another embodiment of a delivery system.
Figure 19:
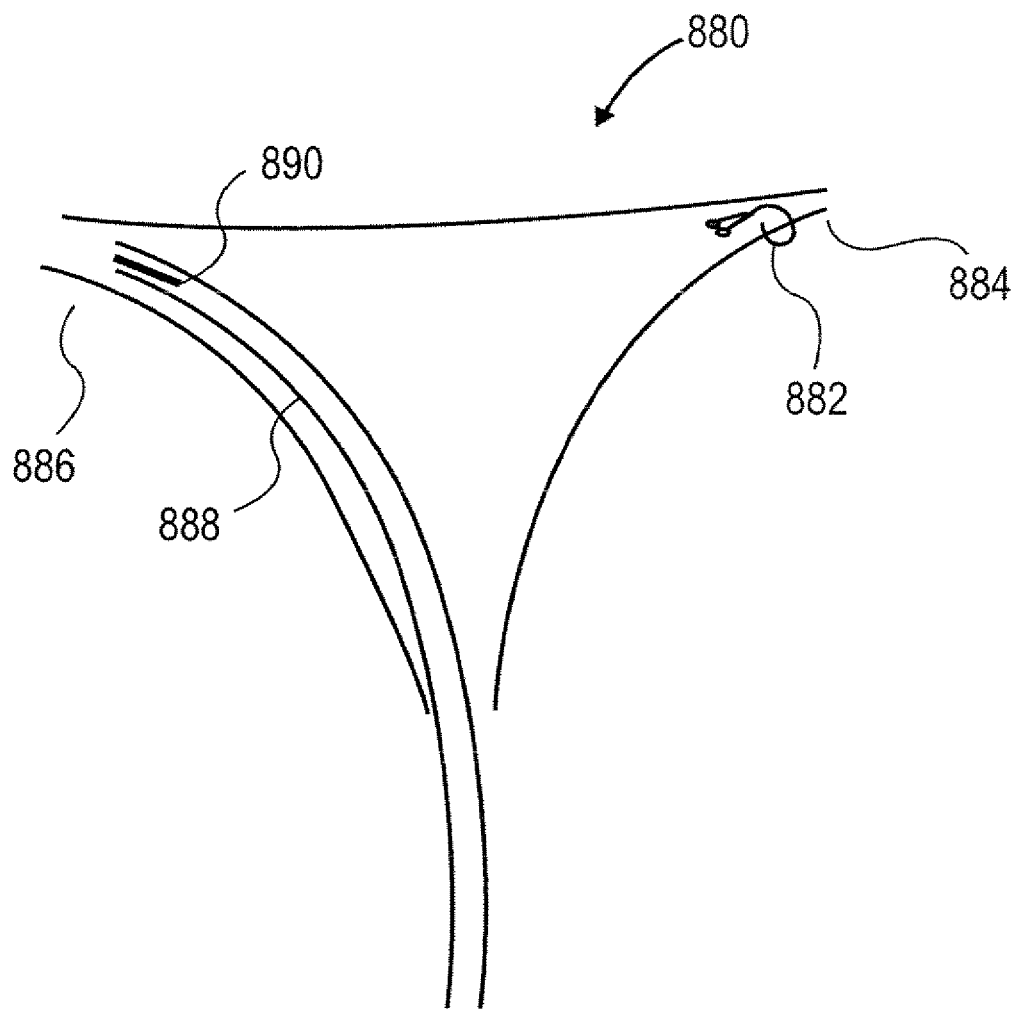
FIG. 19 shows a view of a uterus in which a first insert has been deployed and a second insert is being deployed in a second fallopian tube of the uterus.

FIG. 15 shows a particular embodiment in which a delivery system is capable of delivering two inserts, one for each of the fallopian tubes in a patient. The inserts resemble the insert shown in FIG. 13D or they may resemble the insert shown in FIGS. 14A-14C. Each insert 776 and 777 includes a tissue ingrowth agent (respectively tissue ingrowth agents 788 and 789) and they further include a sharp distal tip which is designed to pierce the fallopian tube. Each insert is disposed within a respective lumen which is housed within a delivery sheath. In particular, the insert 776 is disposed within the lumen 779 which is housed within the delivery sheath 781. The insert 777 is disposed in the lumen 780, which lumen is separated from lumen 779 by its separator 782 which may be a common wall of the two lumens 779 and 780. A first tube 783 is also disposed in the lumen 779 and is used to push out a first insert 776. The first tissue ingrowth agent 788 is disposed within a hollow portion of the first tube 783. The second tissue ingrowth agent 789 is disposed within the hollow portion of the second tube 784 which is within the second lumen 780. It will be appreciated that in one use of the delivery system shown in FIG. 15, a physician may position the distal portion of the delivery system 775 in a position near or inside the fallopian tube and push one of the tubes to push out an insert, such as the first insert. After the first insert has been deployed (e.g. such as in the manner shown in FIG. 14B), the physician may move the delivery system and then position the delivery system in a position near or inside the second fallopian tube and cause the second insert to be deployed by pushing the second tube to thereby deploy the second insert into the second fallopian tube. The diagram showing this method of deploying such inserts is shown in FIG. 19, although it will be appreciated that two separate delivery systems may be used to deploy an insert such as that shown in FIG. 14C or in FIG. 13C, etc. As shown in FIG. 19, a first insert 882 has been implanted into the fallopian tube 884 of the uterus 880 and a second insert 890 is about to be deployed from the delivery system 888 into the second fallopian tube 886.

Figure 16A:
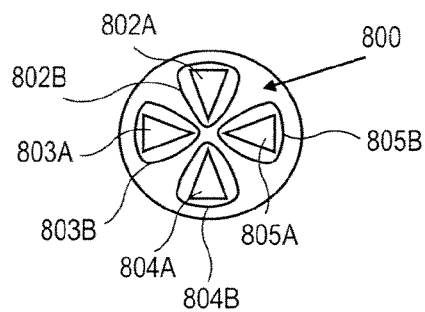
FIG. 16A shows a cross-sectional view of a delivery system which deploys an insert which is similar to the insert shown in FIGS. 14A-14C.
Figure 16B:
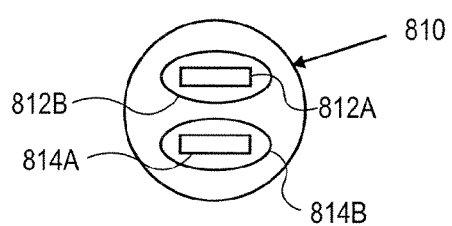
FIG. 16B shows a cross-sectional view of a delivery system which deploys an insert which is similar to the inserts shown in FIGS. 14A-14C.
Figure 16C:
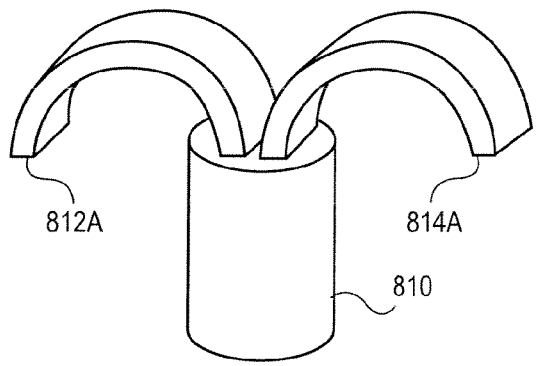
FIG. 16C is a side perspective view of the delivery system shown in FIG. 16B.

FIGS. 16A-16D show several different alternative embodiments of delivery catheters having inserts which are similar to the inserts shown in FIG. 13C or 14C or FIG. 15 or FIG. 13D. The delivery system 800 includes four inserts which may be used in the case where a fallopian tube receives two inserts each rather than a single insert. Each insert is disposed within a lumen and is engagable by a push rod which can be used to push the insert out of the delivery system. Thus the four inserts 802A, 803A, 804A, 805A, are disposed within their respective lumens 802B, 803B, 804B, and 805B. A delivery system 810 includes two inserts which are ribbon-shaped, as opposed to the triangular cross-sectional shape of the inserts shown in the case of FIG. 16A. The ribbon-shaped insert 812A is disposed within a lumen 812B and the ribbon insert 814A is disposed within a lumen 814B. FIG. 16C shows a side perspective view of these two inserts after they have been pushed at least partially out of the delivery lumen 812. It can be seen that the inserts each bend as they are pushed out of their respective delivery lumen, and thus they resemble the manner in which the insert 755 (in FIGS. 14A-14C) or the insert 714 (in FIG. 13C) bend upon or after deployment in a second configuration which is different than a first (e.g. straight) configuration.

Figure 16D:
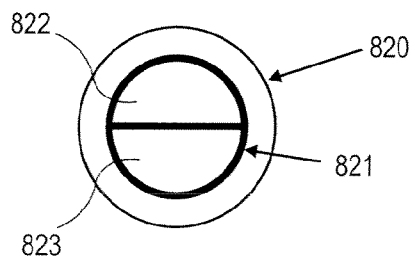
FIG. 16D is a cross-sectional view of another delivery system having inserts which are similar to the insert shown in FIGS. 14A-14C.

FIG. 16D shows another example of a delivery system 820 which includes two inserts 822 and 823 disposed within a single lumen 821. In this case, the cross-sectional shape of each insert resembles a half-moon or half-circle.

Figure 17A:
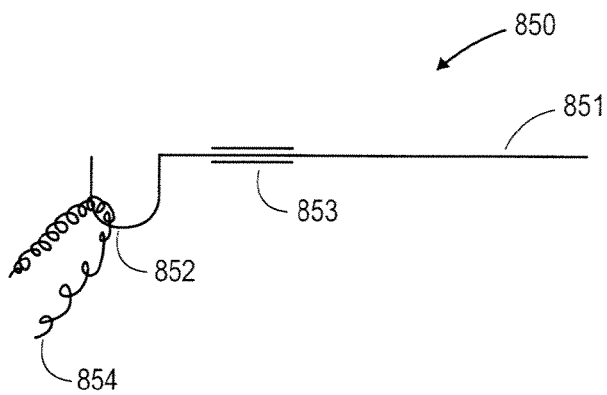
FIG. 17A is a side view of another embodiment of an insert which functions in a manner which is similar to the insert shown in FIGS. 14A-14C; the view of FIG. 17A shows the insert in a first configuration.
Figure 17B:
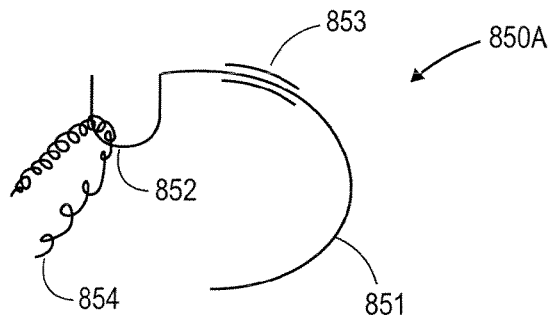
FIG. 17B is a side view of the insert of FIG. 17A which has assumed a second configuration.

FIGS. 17A and 17B show another embodiment of an insert which has a first configuration while it is within a delivery system and has a second configuration upon or after being deployed from the delivery system. The insert 850 includes a shaft 851 and a retaining portion 852. The retaining portion 852 is designed to retain or hold a tissue ingrowth agent 854 which may be a polyester fiber or other type of materials described herein which are designed to elicit a tissue ingrowth, such as the tissue ingrowth 757 shown in FIG. 14C. The insert 850 also includes an imaging marker 853 which may be radiopaque in order to be visible in an X-ray image or it may be a material which would be visible in an ultrasound image. The tissue ingrowth agent 854 may be attached to the retaining portion 852 by any one of (or a combination of) a number of techniques, including an adhesive bond which glues the agent 854 to the portion 852, a needle hole in the portion 852 into which the agent 854 is threaded, a crimp bond wherein the portion 852 is crimped around the agent 854, or a bend in portion 852 which acts like a hook to secure the agent 854 to the portion 852. The insert 850A shown in FIG. 17B shows the second configuration of the insert 850 after it has entered the second configuration. The shaft 851 is in a second configuration which is a curved configuration which is bent in one direction. This is similar to the bending of the insert 750 shown in FIG. 14B. A retaining portion 852 may itself bend although this is not shown in FIG. 17B.

Figure 18D:
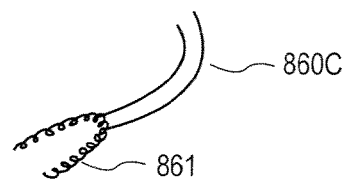
FIG. 18D shows the insert of FIG. 18C after it has assumed a memorized shape, which may be provided by a shape memory material within the insert.
Figure 18E:
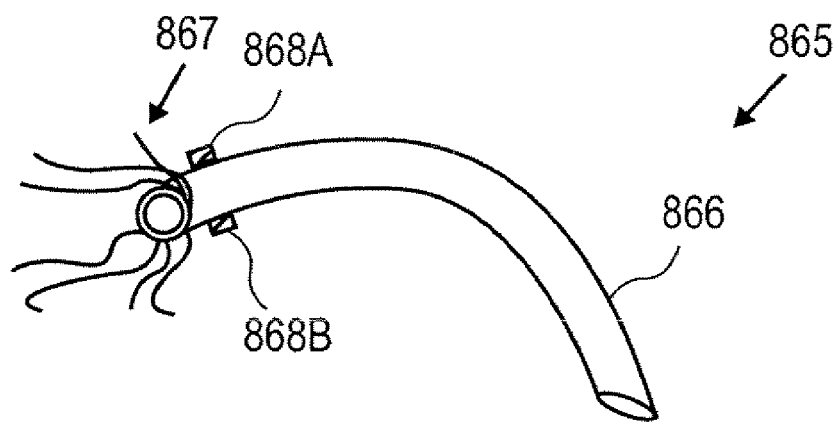
FIGS. 18E and 18F show an example of another insert.
Figure 18F:
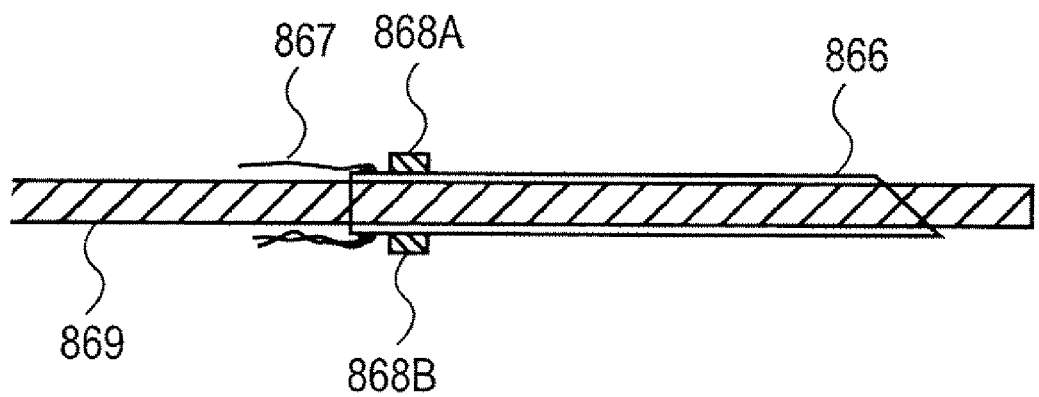

FIG. 18A and its associated FIGS. 18B, 18C and 18D, show another method for making an insert and another structure of an insert. This insert may, like in inserts 776 or 777 or 850 or 755, be pushed out of the delivery system to pierce a portion of the fallopian tube and may change configuration in the process of being pushed out from the first configuration which is substantially straight or some other configuration to a second configuration which is typically a bent configuration which may be bent (e.g. bent proximally or distally) relative to the portion in which the fallopian tube was pierced. The shaft 860 shown in FIG. 18 is a starting material which is bent in half (or in some other portion) to form the bent shaft 860A. A tissue ingrowth agent may then be wrapped around the corner of the bend and may be further secured by a biocompatible adhesive or by tying or other methods or a combination of methods. Then the bent shaft is further bent to achieve the configuration shown in FIG. 8C. Then a shape is formed to create the shape 860C which is the shape of the second configuration of the insert after it has been deployed within the fallopian tube. This shape may be memorized by heat annealing the material which may be a nitinol material or a platinum/iridium composite material which is heat set into the memorized shape. FIGS. 18E and 18F show another exemplary embodiment of an insert. The insert 865, shown in a side view of FIG. 18E, includes a hollow tube 866 which includes a piercing distal end and which includes tissue ingrowth fibers 867 at a proximal end of the insert. The tissue ingrowth fibers may be attached to the hollow tube 866 by, for example, an adhesive. FIG. 18E shows the hollow tube 866 in its deployed configuration which resembles a curve, such as the curved shape of the insert shown in FIG. 18D. The hollow insert 866 also includes handles 868A and 868B which may be used to push the tube 866 out of a delivery system or to otherwise deploy the insert 865. The tube 866 is designed to pierce a wall of the fallopian tube and to bend into a deployed, curved configuration, which keeps the insert anchored in the fallopian tube. FIG. 18F shows a cross-sectional view of tube 866 before it has been deployed. The tube 866, prior to deployment, is kept straight by a straight, removable rod 869 which is disposed in the lumen of the tube 866. The rod 869 is removed by pulling the rod 869 proximally relative to the tube 866. As the rod 869 is removed, the shape memory material in the tube 866 causes the tube 866 to assume a curved shape.

FIGS. 20A-24 will now be referred to in connection with yet another aspect of certain embodiments of the present inventions. This particular aspect relates to the use of a fluid to deploy one or more inserts from a delivery system. In a typical embodiment according to this aspect, one portion of the insert is designed to act generally as a sail and be pushed by the fluid within a delivery lumen and out of the delivery lumen into a portion of the fallopian tube. The insert may include a tissue ingrowth agent such as a Dacron or polyester fiber which is designed to cause a tissue ingrowth such as the tissue ingrowth 757 shown in FIG. 14C. The fluids used may be a liquid or a gas; for example, the liquid may be a phosphate buffered saline. The inserts which may be used with this aspect may include a coil or another mechanism which radially or otherwise expands in a manner to engage the walls of the fallopian tube to lodge the device within the fallopian tube such that the tube cannot expel the device.

Figure 20A:
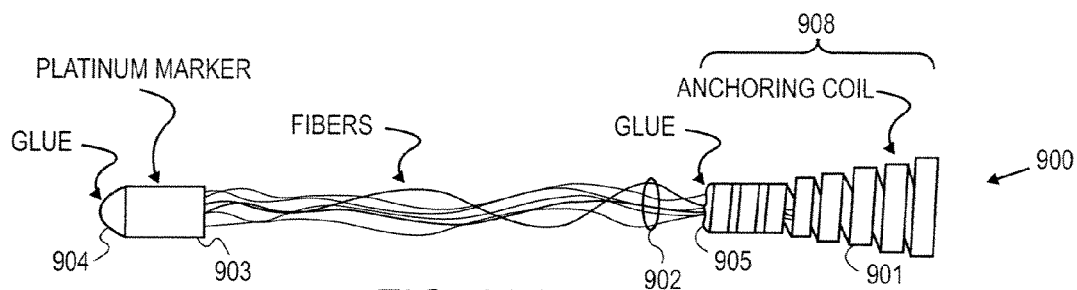
FIG. 20A shows another embodiment of an insert which may be used in various aspects of the inventions.

The insert 900 shown in FIG. 20A includes a proximal end 908 which includes an anchoring coil 901 which is attached to fibers 902 by a proximal connector 905 which may be glue. A distal end 903 of the insert 900 is also attached to the fibers 902 at the distal tip 904 which may include a glue to attach the fibers to the distal tip. The distal end 903 may be a platinum marker which is one form of an imaging marker. The insert is deployed within the lumen which has a fluid input port which is designed to receive a fluid which is used to expel the insert out of the lumen and into a portion of the fallopian tube.

Figure 20B:
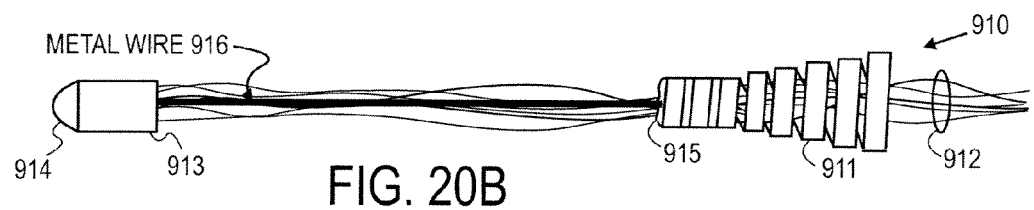
FIG. 20B shows in a side view another exemplary embodiment of an insert which may be used in various aspects of the inventions.

FIG. 20B shows an insert 910 which includes a proximal end 911 through which fibers 912 are disposed. The fibers may be tissue ingrowth agents such as polyester fibers as described above. The proximal end 911 may be a superelastic or shape memory material which is designed to expand to engage the walls of the fallopian tube. A proximal connector.915, which may be glue, couples the fibers 912 to the proximal end 911. A rigid metal wire or semi-rigid metal wire 916 is coupled to the proximal connector 915 and thereby coupled to the proximal end 911. The wire 916 is also coupled to the distal end 913, and the fibers 912 are also coupled to the distal end 913 as shown in FIG. 20B. Rather than a metal wire, the connection between the distal end 913 and the proximal end 911 may be a plastic or other material which is rigid or semi-rigid. This connection tends to keep a separation between the distal and proximal ends as the insert is pushed out by the fluid from the lumen as described herein (and also keeps this separation after the insert has been deployed).

Figure 20C:
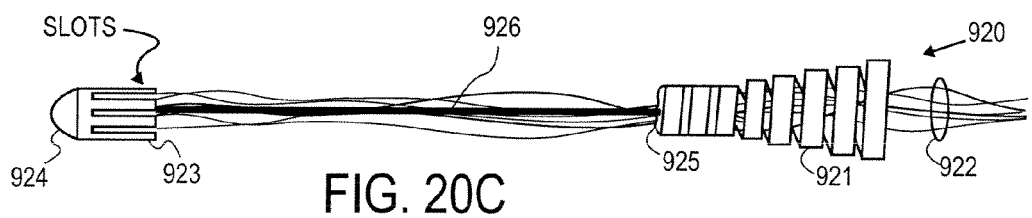
FIG. 20C shows in a side view another exemplary embodiment of an insert which may be used in various aspects of the inventions.

FIG. 20C shows yet another embodiment of an insert, in this case insert 920, which includes a proximal end 921 through which fibers 922 are disposed. A proximal connector 925, which may be glue, attaches the fibers 922 to the proximal end 921. The proximal connector 925 also attaches the metal connector 926 between the distal end 923 and the proximal end 921. The fibers are also coupled to the distal end 923 which includes slots as shown in FIG. 20C. A distal tip, which may be glue 924, is used to secure the connector 926 to the distal end 923 and to secure the fibers 922 to the distal end.

Figure 20D:
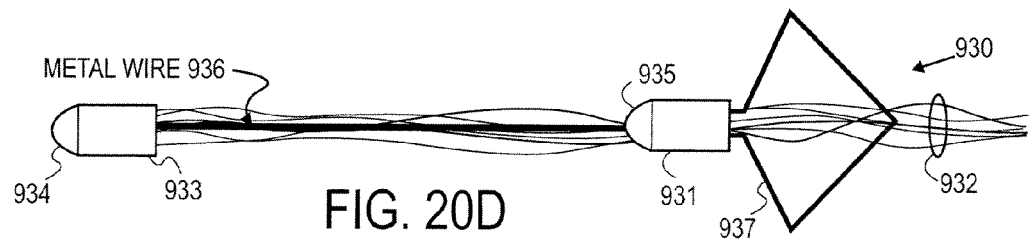
FIG. 20D shows another alternative insert which may be used in various aspects of the inventions.

FIG. 20D shows another insert 930 which also includes fibers 932 disposed between the distal end 933 and a proximal end 931. The proximal connector 935 couples the fibers and the metal connector 936 to the proximal end 931 and a distal tip 934, which may be glue, couples the fibers, which may be tissue ingrowth agents, to the distal end 933. The metal wire 936 may alternatively be another material which is rigid or semi-rigid and which is designed to keep a separation between the distal end and the proximal end during the process of expelling the insert from a lumen using a fluid and while the insert is positioned in the fallopian tube during the tissue ingrowth process. The insert 930 further includes proximal wings 937 which may have a first narrow configuration designed to fit within the lumen of the delivery system during deployment and a second configuration which expands radially after the device has been deployed.

Figure 20E:
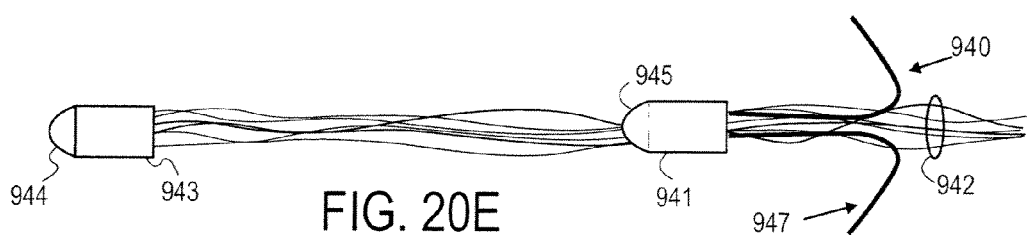
FIG. 20E shows another exemplary embodiment of an insert which may be used in various aspects of the inventions.

FIG. 20E shows a device which includes proximal wings 947 which operate in a similar fashion in that they have a reduced size configuration and an enlarged size configuration which exists after deployment of the insert 940. This insert also includes a proximal end 941 which is coupled to fibers 942. The fibers are also coupled to a distal end 943 which has a distal tip 944 which may be glue which is used to attach the fibers 942 between the distal end 943 and the proximal end 941. It can be seen that the embodiments shown in FIGS. 20A and 20E do not include a metal wire or an other rigid or semi-rigid structure which is used to keep the two ends separated during deployment and after deployment. It will be appreciated, however, that these embodiments may use such a connector between the two ends.

Figure 20F:
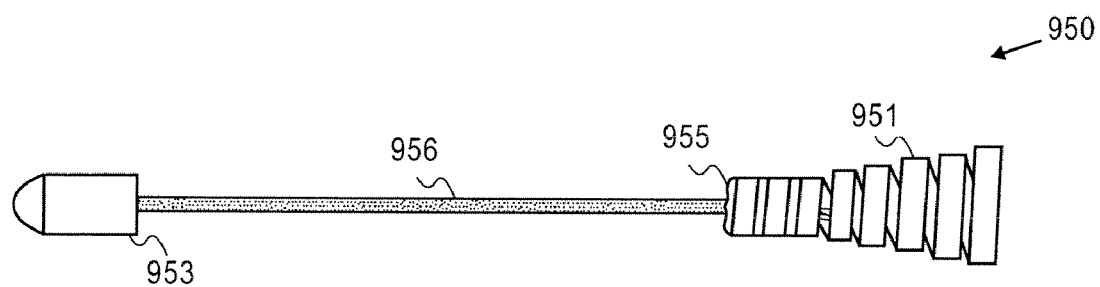
FIG. 20F shows another insert which may be used in various aspects of the inventions.

FIG. 20F shows an embodiment without fibers. In this case, the material of one of the elements of the insert may be made out of a tissue ingrowth agent, such as a polyester or may be impregnated with microscopic fibers which are designed to elicit a tissue ingrowth. The insert of FIG. 20F includes a proximal end 950 which may be made out of a shape memory material or a superelastic material such as nitinol. The proximal end is coupled to a metal connector or other connector 956 by a proximal connector 955. The distal end 953 is also coupled to the metal connector.

Figure 21:
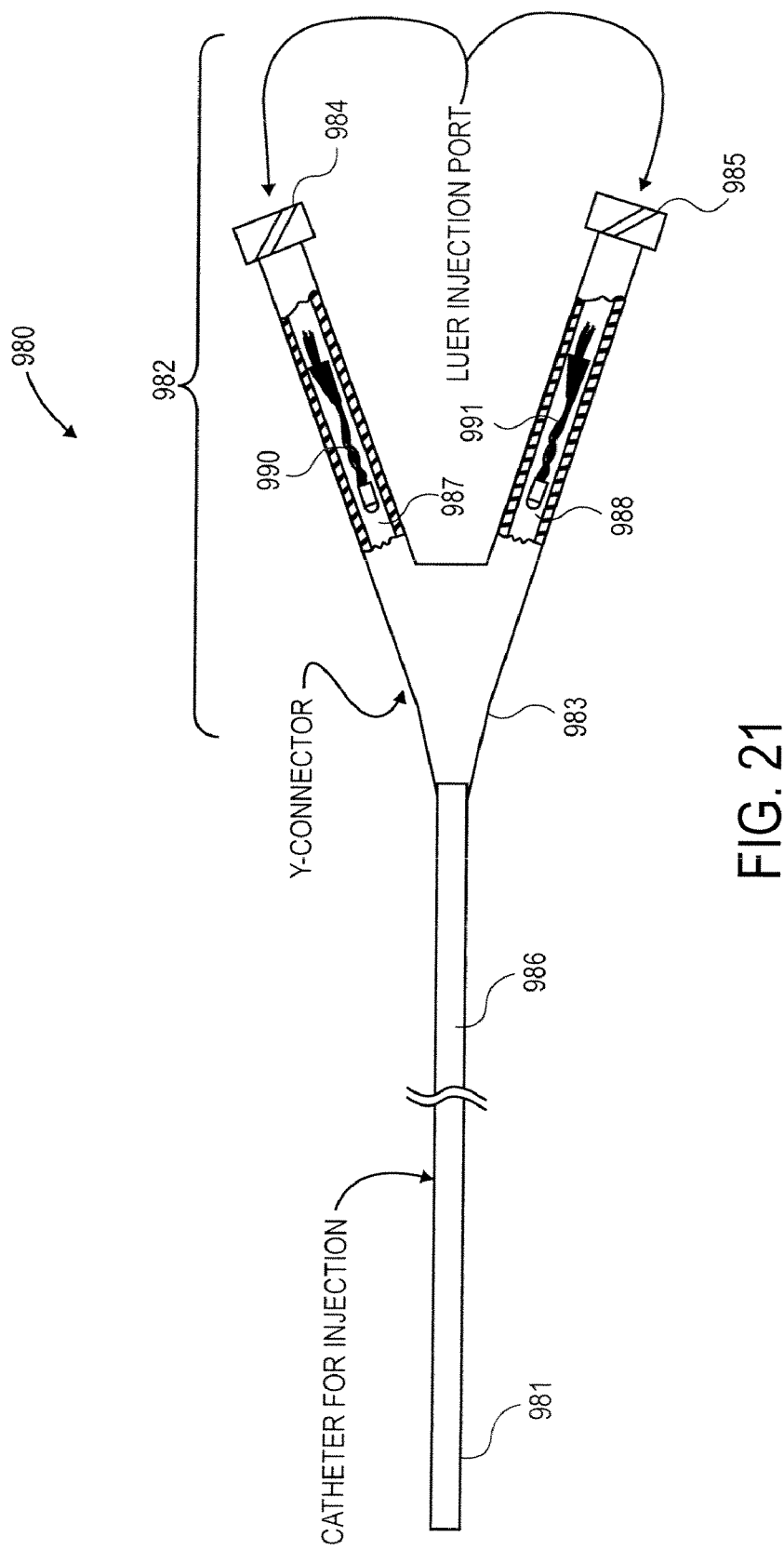
FIG. 21 shows a delivery system which may be used in deploying various different kinds of inserts, such as the inserts shown in FIGS. 20A-20F.

FIG. 21 shows an example of a delivery system 980 which may use one of the various inserts such as those shown in FIGS. 20A-20F. The delivery system 980 includes a proximal portion 982 which includes a first input port 984 which may be a first fluid input port and a second input port 985 which may be a second fluid input port. These input ports are in turn coupled to a first lumen 987 and a second lumen 988 respectively as shown in FIG. 21. A first insert 990 is disposed within the first lumen 987 and a second insert 991 is disposed within the second lumen 988. A Y connector 983 couples the output from these first and second lumens to the middle section 986 of the delivery system which in turn is coupled to or continuous with (as one integrated piece) the distal end 981. The first and second inserts may be expelled by introducing a fluid through the fluid input ports of the respective lumens. For example, a syringe may be attached to the input port 984 and fluid within the syringe may be expelled through the syringe and into the lumen 987 forcing the first insert 990 into the Y connector and then down toward the distal end 981 and finally out of the distal end and into the fallopian tube. Similarly, the second insert 991 may be expelled by connecting a syringe to the second input port 985 and by introducing a fluid from that syringe or from another device into the second lumen 988 thereby forcing the second insert 991 through the Y connector 983 and down through the distal end 981 and out of the delivery system into a second fallopian tube.

FIGS. 22A and 22B show that the anchoring coil used in the various embodiments shown in FIGS. 20A, 20B, 20C, and 20F may employ a radially expanding or otherwise expanding coil which is designed to expand after deployment to engage the walls of the fallopian tube. The distal end 1001 of the coil may not expand as much as the other end which expands from a diameter D1 to a larger diameter D2 shown in the expanded coil 1000A of FIG. 22B. (Also see a similar behavior in the coil at the proximal end of FIG. 20B.)

The fluid delivery system described herein provides certain advantages relative to other types of delivery systems for delivering an insert or an implant into a fallopian tube. In particular, the fluid delivery system may tend to open an otherwise closed or substantially closed fallopian tubes, such as the fallopian tube 1040 as shown in FIG. 23A which is a cross-sectional view of the tube. The introduction of fluid will tend to open the fallopian tube to a more open configuration 1040A as shown in FIG. 23B which is a cross-sectional view of the tube. The other delivery systems described herein may also provide this ability to open a closed or substantially closed fallopian tube.

Figure 24:
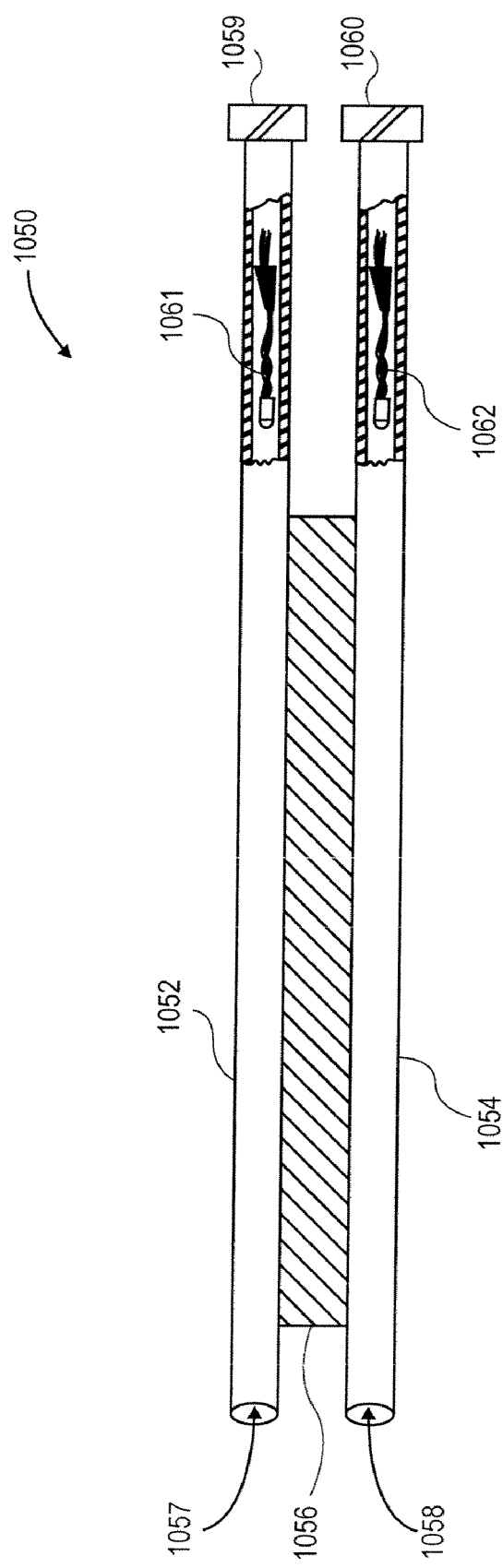
FIG. 24 shows a side view, with a partial cutaway view, of a delivery system which may be used to deploy various different inserts, such as the inserts shown in FIGS. 20A-20F.

FIG. 24 shows an alternative embodiment of a delivery system which uses two separate lumens which are not connected, unlike the arrangement shown in FIG. 21. In the embodiment of FIG. 24, two separate lumens 1057 and 1058 are designed to deliver the two inserts 1061 and 1062 respectively. These inserts may be similar to any one of the various inserts shown in FIGS. 20A-20F. It will be appreciated that these inserts may also be comprised at least partially of molded materials or extruded materials which are made out of polymers as described above. The first and second inserts 1061 and 1062 may be expelled by injecting a fluid, such as a phosphate buffered saline or a gas into the respective injection ports 1059 and 1060 as shown in FIG. 24. This fluid causes the respective insert to sail through the lumen defined by the respective tubes 1052 and 1054 and out of the lumen. The catheter 1050 shown in FIG. 24 also includes a tube separator 1056 which is one of many possible configurations which may be employed to join the two delivery tubes 1052 and 1054. In an alternative embodiment, a multi-lumen catheter within a delivery sheath may be used to deliver two separate inserts.

It will be appreciated that the various devices described herein may be used for other purposes, including medical purposes, such as the treatment of aneurysms or the occlusion of other biological lumens or may be used as a male contraceptive (as an alternative to a vasectomy) by occluding a portion of the vas deferens. Further, other alternative embodiments may utilize surgical staples with a tissue ingrowth agent wherein one or more surgical staples may be implanted into a fallopian tube to cause a functional occlusion of the tube to provide a permanent contraception.

While the exemplary embodiment of the present invention has been described in some detail for clarity of understanding and by way of example, a variety of adaptations, changes and modifications will be obvious to those who are skilled in the art. Hence the scope of the present invention is limited solely by the following claims.

What is claimed is:

1. A method of inhibiting conception in a patient having a first fallopian tube and a second fallopian tube, said method comprising:

introducing a delivery system transcervically into a first fallopian tube, said delivery system having a first insert which is removably coupled to said delivery system and which is designed to be deployed within a portion of said first fallopian tube;

expelling said first insert from said delivery system, wherein said first insert becomes deployed and wherein said first insert is formed at least in part from a non-biodegradable material;

introducing said delivery system into a second fallopian tube, said delivery system having a second insert which is removably coupled to said delivery system and which is designed to be deployed within a portion of said second fallopian tube;

expelling said second insert from said delivery system, wherein said second insert becomes deployed and wherein said second insert is formed at least in part from a non-biodegradable material;

wherein said delivery system comprises:

an outer sheath;

a delivery catheter coaxially disposed within said outer sheath;

a lumen disposed within said delivery catheter, said first insert and said second insert being serially disposed within said lumen; and wherein a biodegradable separator separates said first insert from said second insert within said lumen, and wherein said biodegradable separator is expelled into the first or second fallopian tube.

2. A method as in claim 1 wherein said delivery system further comprises a third insert removably coupled to said delivery system.

3. A method as in claim 1 wherein each of said first insert and said second insert comprises a polymer which is either molded or extruded.

4. A method as in claim 3 wherein said polymer comprises an organic material and wherein each of said first insert and said second insert comprises a resilient, expandable metal.

5. A method as in claim 1 further comprising:

operating a first proximal control to expel said first insert;

operating a second proximal control to expel said second insert; and wherein a fluid is used to expel said first insert and said second insert.

6. A method as in claim 1 further comprising:

operating a first proximal control to expel said first insert;

operating said second proximal control to expel said second insert.

7. A method as in claim 1 wherein said first insert and said second insert each comprise a generally tubular, resiliently expandable frame having openings and a substantially hollow core and a tissue activating material disposed in said substantially hollow core.

8. A method as in claim 7 wherein said frame comprises a superelastic material.

9. A method as in claim 1 further comprising:

unpackaging a kit containing instructions and said delivery system which is loaded with said first insert and said second insert and wherein, prior to said unpackaging, said delivery system is packaged and sterilized in packaging which maintains the sterility of said delivery system for a period of time.

10. A medical device comprising;

a delivery system;

a first insert removably coupled to said delivery system, said first insert being designed to be deployed within a portion of a first fallopian tube and being formed at least in part from a non-biodegradable material;

a second insert removably coupled to said delivery system, said second insert being designed to be deployed within a portion of a second fallopian tube and being formed at least in part from a non-biodegradable material;

a first lumen coupled to said delivery system and configured to release the first insert;

a second lumen coupled to said delivery system and configured to release the second insert, wherein the first and second lumen are not co-axial;

a first fluid input port coupled to said first lumen, said first fluid input port being designed to receive a fluid to expel said first insert from said first lumen;

a second fluid input port coupled to said second lumen, said second fluid input port being designed to receive a fluid to expel said second insert from said second lumen.

11. A medical device as in claim 10 wherein said delivery system comprises an outlet lumen having an outlet and wherein said outlet lumen is coupled to said first lumen and to said second lumen and wherein said first insert and said second insert are expelled through said outlet of said outlet lumen.

12. A medical device as in claim 10 wherein said first lumen comprises a first outlet and said second lumen comprises a second outlet and wherein said first insert is expelled through said first outlet and said second insert is expelled though said second outlet.

* * * * *